(12) United States Patent
Boletta et al.

(10) Patent No.: US 10,478,446 B2
(45) Date of Patent: Nov. 19, 2019

(54) COMPOUNDS FOR USE IN POLYCYSTIC KIDNEY DISEASE

(71) Applicants: FONDAZIONE CENTRO SAN RAFFAELE OFFICE OF BIOTECHNOLOGY TRANSFER, Milan (IT); FONDAZIONE TELETHON, Rome (IT)

(72) Inventors: Alessandra Boletta, Milan (IT); Marco Chiaravalli, Milan (IT); Isaline Severine Marie-Josephe Rowe, Milan (IT)

(73) Assignees: FONDAZIONE CENTRO SAN RAFFAELE OFFICE OF BIOTECHNOLOGY TRANSFER, Milan (IT); FONDAZIONE TELETHON, Rome (IT)

( * ) Notice: Subject to any disclaimer, the term of this patent is extended or adjusted under 35 U.S.C. 154(b) by 0 days.

(21) Appl. No.: 14/413,280

(22) PCT Filed: Jul. 3, 2013

(86) PCT No.: PCT/EP2013/064036
§ 371 (c)(1),
(2) Date: Jan. 7, 2015

(87) PCT Pub. No.: WO2014/006093
PCT Pub. Date: Jan. 9, 2014

(65) Prior Publication Data
US 2015/0297620 A1 Oct. 22, 2015

Related U.S. Application Data

(60) Provisional application No. 61/667,615, filed on Jul. 3, 2012.

(51) Int. Cl.
| | | |
|---|---|---|
| *A61K 31/7004* | (2006.01) |
| *A61K 31/7008* | (2006.01) |
| *A61K 45/06* | (2006.01) |
| *A61K 31/436* | (2006.01) |
| *A61K 31/155* | (2006.01) |
| *A61K 31/352* | (2006.01) |
| *A61K 31/437* | (2006.01) |
| *A61K 31/44* | (2006.01) |

(52) U.S. Cl.
CPC ........ *A61K 31/7008* (2013.01); *A61K 31/155* (2013.01); *A61K 31/352* (2013.01); *A61K 31/436* (2013.01); *A61K 31/437* (2013.01); *A61K 31/44* (2013.01); *A61K 31/7004* (2013.01); *A61K 45/06* (2013.01)

(58) Field of Classification Search
CPC ................ A61K 31/155; A61K 31/352; A61K 31/435; A61K 31/44; A61K 31/31; A61K 31/7004; A61K 31/7008; A61K 2300/00
USPC .................... 514/23; 536/1.11, 122, 18.7, 54
See application file for complete search history.

(56) References Cited

FOREIGN PATENT DOCUMENTS

CN 102225201 A * 10/2011 .............. A61P 27/02

OTHER PUBLICATIONS

National Organization of Rare Disorders, NORD, 2005, p. 1-5.*
Wilson et al, Biochim. Biophys. Acta, 2006, 1762, 647-655.*
Harris et al, Annu. Rev. Med. 2009, 60, 321-337.*
Wilson, "Polycystic Kidney Disease", New England Journal of Medicine, 2004, vol. 350, No. 2, pp. 151-164.
Everson, "Polycystic Liver Disease", Gastroentereology & Hepatology, 2008, vol. 4, issue 3, pp. 179-181.

* cited by examiner

*Primary Examiner* — Ganapathy Krishnan
(74) *Attorney, Agent, or Firm* — Lucas & Mercanti, LLP

(57) ABSTRACT

Polycystic kidney disease is a cystic genetic disorder of the kidneys. Recent identification of signaling cascades deregulated in PKD has led to the initiation of several clinical trials, but an effective therapy is still lacking. A new therapeutic paradigm is capable of improving the proliferation rate and cystic kidney volume in PKD.

11 Claims, 16 Drawing Sheets

Figure 1:
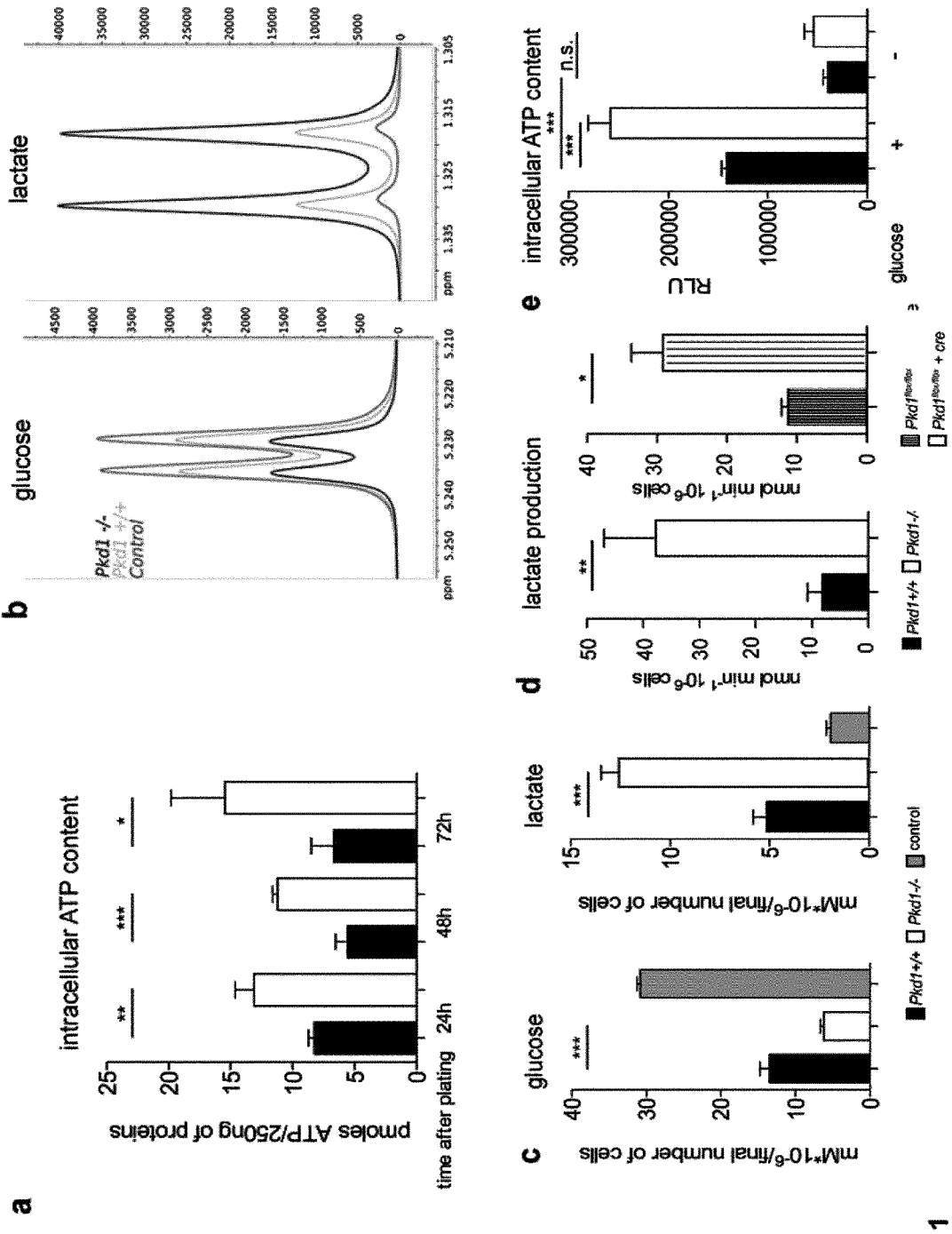
Figure 1:
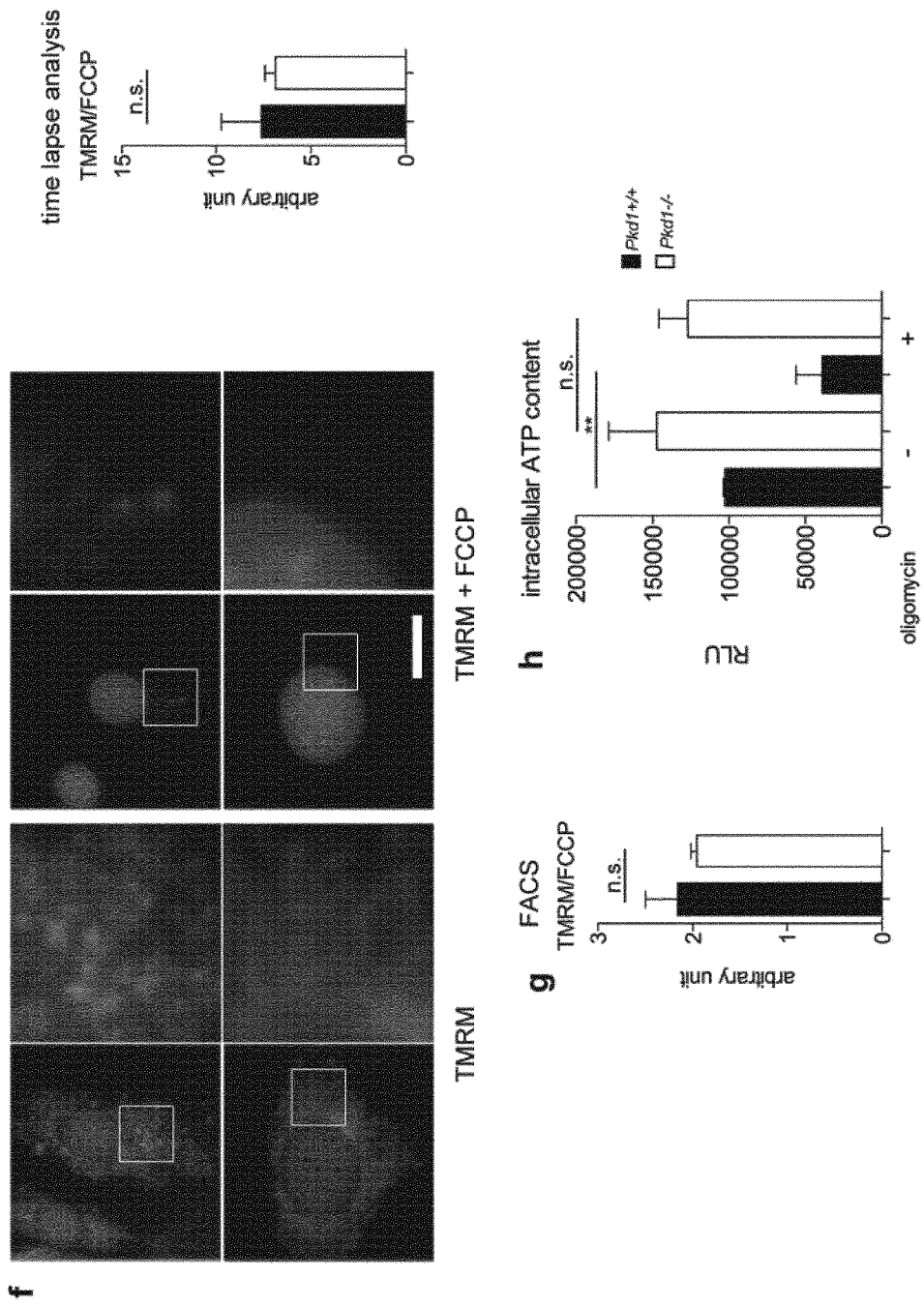

Specification includes a Sequence Listing.

| metabolite | a peak used for quantification (ppm) | b $Pkd1^{+/+}$ (mM·10⁻⁶/cell) | b $Pkd1^{-/-}$ (mM·10⁻⁶/cell) | c $Pkd1^{+/+}_{rel}$ | c $Pkd1^{-/-}_{rel}$ | d t-test ($Pkd1^{+/+}/Pkd1^{-/-}$) |
|---|---|---|---|---|---|---|
| glucose | 5.24-5.23 e(d) alpha<br>3.26-3.23 e (t) beta | 13.54 (0.20) | 6.27 (0.08) | -0.24 | -0.59 | *** |
| lactate | 4.13-4.10 e(q) | 5.31 (0.10) | 12.80 (0.25) | 3.61 | 12.25 | *** |
| pyruvate | 2.37 e(s) | 0.0998 (0.0019) | 0.033 (0.0002) | 25.47 | 9.39 | *** |
| succinate | 2.40 e(s) | 0.2628 (0.0021) | 0.2252 (0.0078) | -0.03 | -0.02 | ns |
| choline | 3.20 e(s) | 0.0108 (0.0002) | 0.0095 (0.0002) | -0.67 | -0.63 | ** |
| formate | 8.45 e(s) | 0.0947 (0.0018) | 0.0901 (0.0006) | 2.87 | 3.41 | *** |
| ethanol | 3.68-3.66 e(q) | 0.440 (0.003) | 0.399 (0.013) | -0.16 | -0.11 | ns |
| alanine | 1.48-1.47 e(d) | 0.23 (0.01) | 0.279 (0.002) | 0.39 | 0.98 | *** |
| arginine | 1.67-1.60 e(m) | 0.325 (0.003) | 0.251 (0.009) | -0.29 | -0.21 | ns |
| glutamate | 2.36-2.33 e(m) | 0.132 (0.002) | 0.246 (0.007) | 0.11 | 1.52 | *** |
| glutamine | 2.21-2.06 e(m) | 1.900 (0.020) | 1.800 (0.050) | -0.57 | -0.60 | ns |
| glycine | 3.56 e(s) | 0.384 (0.007) | 0.277 (0.005) | 0.28 | 0.07 | *** |
| histidine | 7.09 e(s) | 0.155 (0.002) | 0.122 (0.003) | -0.14 | -0.19 | ns |
| isoleucine | 1.01-1.00 e(d)<br>0.95-0.92 e(t) | 0.474 (0.003) | 0.358 (0.006) | -0.19 | -0.20 | ns |
| leucine | 0.97-0.95 e(t) | 0.386 (0.003) | 0.319 (0.012) | -0.28 | -0.29 | ns |
| lysine | 3.07-3.04 e(m) | 0.500 (0.002) | 0.428 (0.006) | -0.14 | -0.14 | ns |
| methionine | 2.65-2.63 e(t) | 0.1018 (0.0005) | 0.0902 (0.0012) | 0.47 | 0.57 | ns |
| phenylalanine | 7.44-7.43-7.41 e(m) | 0.281 (0.002) | 0.225 (0.001) | -0.16 | -0.16 | ns |
| threonine | 3.59-3.58 e(t) | 0.700 (0.009) | 0.583 (0.004) | -0.08 | -0.11 | ns |
| tryptophan | 7.74-7.72 e(d) | 0.064 (0.003) | 0.059 (0.002) | -0.13 | -0.03 | ns |
| tyrosine | 7.20-7.18 e(m or d) | 0.286 (0.002) | 0.220 (0.002) | -0.58 | -0.58 | ns |
| valine | 1.04-1.03 e(d)<br>0.99-0.98 e(d) | 0.435 (0.005) | 0.348 (0.009) | -0.20 | -0.21 | ns | a. Peaks were referenced to DSS peak at 0.00ppm. Spectra were deconvolved with GSD (see Materials and Methods). More than one region per metabolite was chosen for quantification. Each area was calculated and then divided by the number of protons contributing to the integrated peaks. For glucose the anomeric proton was analysed considering the sum of the two doublets signal corresponding to alpha and beta isomers. The number of ¹H nuclei contributing to signals was taken into account for normalization.

b. Standard deviation are reported in parenthesis. For WT and KO conditions three biological replicas were prepared and split into three technical replicas each, which were next analysed by NMR. For control conditions (CTR) only the three technical replicas were considered. Average values and standard deviations have been calculated among the technical replicas, weighted averages (with the corresponding standard deviations) were calculated among the biological replicas. As $Pkd1^{+/+}$ and $Pkd1^{-/-}$ cells, despite being seeded in equal amounts, had different growth rates, we decided to normalize integral areas taking into account the number of cells after 24hours incubation.

c. Relative quantification of metabolites was performed using the non conditioned medium as reference (CTR) (equation 1).

$$eq.\ 1\ Rel.Quant_i = \frac{Conc_i[X] \times Conc_i[CTR]}{Conc_i[CTR]}$$

where $Rel.Quant_i$ is the relative quantification of metabolite i; $Conc_i$ is the absolute concentration of each metabolite; X represents WT or KO condition. Negative values reflect metabolites that are up-taken from the medium, whereas positive values reflect metabolites that are released in the medium.

d. T-test was performed between WT and KO conditions (* p<0.05, p<0.01, *p<0.001, ns: not significant)
e. s (singlet), d (double), t (triplet), q (quartet), m (multiplet) denote peak multiplicity

Supplementary Table S1. Metabolic profiling of $Pkd1^{+/+}$ $Pkd1^{-/-}$ cells

Figure 10

Glycolytic gene expression in cystic compared to normal kidneys

| | probe set | gene | Accession | LocusLink | Description | Mean cyst | Mean MCT | Mean kid | fold change (cyst/MCT) | fold change (cyst/Kid) |
|---|---|---|---|---|---|---|---|---|---|---|
| up | 200697_at | HK1 | NM_000188 /// NM_033496 /// NM_033497 /// NM_033498 /// NM_033500 | 3098 | hexokinase 1 | 1175,5 | 707,4 | 680,5 | 1,66 | 1,73 |
| up | 200650_s_at | LDHA | NM_001135239 /// NM_001165414 /// NM_001165415 /// NM_001165416 /// NM_005566 /// NR_028500 | 3939 | lactate dehydrogenase A | 12513,6 | 9028,4 | 8900,5 | 1,39 | 1,41 |
| up | 210041_s_at | PGM3 | NM_015599 | 5238 | phosphoglucomutase 3 | 214,0 | 113,6 | 103,1 | 1,88 | 2,08 |
| up | 201313_at | ENO2 | NM_001975 | 2026 | enolase 2 (gamma, neuronal) | 430,5 | 72,6 | 48,6 | 5,93 | 8,85 |
| up | 201251_at | PKM2 | NM_002654 /// NM_182470 /// NM_182471 | 5315 | pyruvate kinase, muscle | 970,9 | 591,1 | 364,6 | 1,64 | 2,66 |
| up | 202022_at | ALDOC | NM_005165 | 230 | aldolase C, fructose-bisphosphate | 404,8 | 108,1 | 119,3 | 3,75 | 3,39 |
| up | 201968_s_at | PGM1 | NM_001172818 /// NM_001172819 /// NM_002633 | 5236 | phosphoglucomutase 1 | 1980,7 | 1415,2 | 2164,9 | 1,40 | 0,91 |
| up | 200966_x_at | ALDOA | NM_000034 /// NM_001127617 /// NM_184043 | 226 | aldolase A, fructose-bisphosphate | 6608,3 | 4496,3 | 4445,0 | 1,47 | 1,49 |
| up | 214687_x_at | ALDOA | NM_000034 /// NM_001127617 /// NM_184043 | 226 | aldolase A, fructose-bisphosphate | 6456,8 | 4147,2 | 4038,3 | 1,56 | 1,60 |
| up | 238996_x_at | ALDOA | NM_000034 /// NM_001127617 /// NM_184043 | 226 | aldolase A, fructose-bisphosphate | 716,1 | 290,3 | 302,4 | 2,47 | 2,37 |
| up | 226452_at | PDK1 | NM_002610 | 5163 | pyruvate dehydrogenase kinase, isozyme 1 | 432,0 | 131,1 | 152,4 | 3,30 | 2,83 |
| NC | 201250_s_at | SLC2A1 (GLUT1) | NM_006516 | 6513 | solute carrier family 2 (facilitated glucose transporter), member 1 | | | | | |
| NC | 225367_at | PGM2 | NM_018290 | 55276 | phosphoglucomutase 2 | | | | | |
| NC | 223738_s_at | PGM2 | NM_018290 | 55276 | phosphoglucomutase 2 | | | | | |
| NC | 211167_s_at | GCK | NM_000162 /// NM_033507 /// NM_033508 | 2645 | glucokinase (hexokinase 4) | 79,3 | 55,6 | 60,5 | | |
| NC | 202934_at | HK2 | NM_000189 | 3099 | hexokinase 2 | 445,3 | 72,1 | 66,2 | | |
| NC | 222305_at | HK2 | NM_000189 | 3099 | hexokinase 2 | 40,9 | 34,4 | 35,9 | | |
| NC | 208308_s_at | GPI | NM_000175 /// NM_001184722 | 2821 | glucose-6-phosphate isomerase | 1623,3 | 1171,1 | 1327,1 | | |
| NC | 201037_at | PFKP | NM_002627 | 5214 | phosphofructokinase, platelet | 941,1 | 740,3 | 551,3 | | |
| NC | 240202_x_at | PFKP | NM_002627 | 5214 | phosphofructokinase, platelet | 26,7 | 34,8 | 31,3 | | |
| NC | 205936_s_at | HK3 | NM_002115 | 3101 | hexokinase 3 (white cell) | 87,9 | 76,0 | 71,7 | | |
| NC | 200738_s_at | PGK1 | NM_000291 | 5230 | phosphoglycerate kinase 1 | 6997,4 | 6398,8 | 7799,7 | | |
| NC | 200737_at | PGK1 | NM_000291 | 5230 | phosphoglycerate kinase 1 | 1918,4 | 1664,0 | 1971,4 | | |
| NC | 217356_s_at | PGK1 | NM_000291 | 5230 | phosphoglycerate kinase 1 | 1004,6 | 870,9 | 967,7 | | |
| NC | 227068_at | PGK1 | NM_000291 | 5230 | phosphoglycerate kinase 1 | 338,6 | 370,0 | 628,6 | | |
| NC | 212581_x_at | GAPDH | NM_002046 | 2597 | glyceraldehyde-3-phosphate dehydrogenase | 10752,4 | 9762,4 | 11820,5 | | |
| NC | AFFX-HUMGAPDH/M33197_3_at | GAPDH | NM_002046 | 2597 | glyceraldehyde-3-phosphate dehydrogenase | 11031,2 | 10395,86 | 11988, | | |
| NC | 213453_x_at | GAPDH | NM_002046 | 2597 | glyceraldehyde-3-phosphate dehydrogenase | 9114,1 | 7943,4 | 9236,1 | | |
| NC | 217398_x_at | GAPDH | NM_002046 | 2597 | glyceraldehyde-3-phosphate dehydrogenase | 8335,5 | 7254,1 | 9087,8 | | |
| NC | AFFX-HUMGAPDH/M33197_M_at | GAPDH | NM_002046 | 2597 | glyceraldehyde-3-phosphate dehydrogenase | 7307,4 | 5961,9 | 7053,5 | | |
| NC | AFFX-HUMGAPDH/M33197_5_at | GAPDH | NM_002046 | 2597 | glyceraldehyde-3-phosphate dehydrogenase | 2750,4 | 2695,9 | 3264,0 | | |

Figure 11

| | probe set | gene | Accession | LocusLink | Description | Mean cyst | Mean MCT | Mean kid | fold change (cyst/MCT) | fold change (cyst/Kid) |
|---|---|---|---|---|---|---|---|---|---|---|
| NC | 200822_x_at | TPI1 | NM_000365 /// NM_001159287 /// NR_027483 | 7167 | triosephosphate isomerase 1 | 3152,5 | 3049,5 | 4368,4 | | |
| NC | 213011_s_at | TPI1 | NM_000365 /// NM_001159287 /// NR_027483 | 7167 | triosephosphate isomerase 1 | 3147,2 | 3119,7 | 4267,2 | | |
| NC | 210050_at | TPI1 | NM_000365 /// NM_001159287 /// NR_027483 | 7167 | triosephosphate isomerase 1 | 15,6 | 12,6 | 14,5 | | |
| NC | 206844_at | FBP2 | NM_003837 | 8789 | fructose-1,6-bisphosphatase 2 | 23,9 | 24,5 | 28,8 | | |
| NC | 201231_s_at | ENO1 | NM_001428 | 2023 | enolase 1, (alpha) | 3783,5 | 4045,5 | 3600,0 | | |
| NC | 217294_s_at | ENO1 | NM_001428 | 2023 | enolase 1, (alpha) | 143,2 | 184,9 | 232,6 | | |
| NC | 210712_at | LDHAL6B | NM_033195 | 92483 | lactate dehydrogenase A-like 6B | 11,1 | 11,4 | 12,8 | | |
| NC | 204483_at | ENO3 | NM_001976 /// NM_053013 | 2027 | enolase 3 (beta, muscle) | 66,0 | 74,3 | 88,6 | | |
| NC | 211065_x_at | PFKL | NM_002626 /// NR_024108 | 5211 | phosphofructokinase, liver | 378,3 | 417,8 | 469,1 | | |
| NC | 201102_s_at | PFKL | NM_002626 /// NR_024108 | 5211 | phosphofructokinase, liver | 365,7 | 395,0 | 352,6 | | |
| f | 211023_at | PDHB | NM_000925 /// NM_001173468 /// NR_033384 | 5162 | pyruvate dehydrogenase (lipoamide) beta | 2094,3 | 2389,2 | 3226,7 | | |
| NC | 208911_s_at | PDHB | NM_000925 /// NM_001173468 /// NR_033384 | 5162 | pyruvate dehydrogenase (lipoamide) beta | 953,8 | 1035,4 | 1340,5 | | |
| | | | | 16028 | | | | | | |
| NC | 1553888_at | LDHAL6A | NM_001144071 /// NM_144972 | 7 | lactate dehydrogenase A-like 6A | 27,5 | 31,1 | 33,7 | | |
| NC | 212453_at | G6PC2 | NM_001081686 /// NM_021176 | 57818 | glucose-6-phosphatase, catalytic, 2 | 20,8 | 24,2 | 25,5 | | |
| NC | 207858_s_at | PKLR | NM_000298 /// NM_181871 | 5313 | pyruvate kinase, liver and RBC | 36,0 | 72,6 | 75,2 | | |
| NC | 222078_at | PKLR | NM_000298 /// NM_181871 | 5313 | pyruvate kinase, liver and RBC | 34,4 | 72,2 | 118,7 | | |
| NC | 210451_at | PKLR | NM_000298 /// NM_181871 | 5313 | pyruvate kinase, liver and RBC | 20,0 | 44,6 | 105,9 | | |
| down | 203502_at | BPGM | NM_001724 /// NM_199186 | 669 | 2,3-bisphosphoglycerate mutase | 184,2 | 369,8 | 533,1 | -2,0 | -2,9 |
| down | 210976_s_at | PFKM | NM_000289 /// NM_001166686 /// NM_001166687 /// NM_001166688 | 5213 | phosphofructokinase, muscle | 1005,7 | 1280,6 | 1600,1 | -1,3 | -1,6 |
| down | 206952_at | G6PC | NM_000151 | 2538 | glucose-6-phosphatase, catalytic subunit | 8,4 | 61,6 | 924,3 | -7,3 | -109,5 |
| down | 234974_at | GALM | NM_138801 | 130589 | galactose mutarotase (aldose 1-epimerase) | 370,5 | 578,0 | 1025,6 | -1,6 | -2,8 |
| down | 235256_s_at | GALM | NM_138801 | 130589 | galactose mutarotase (aldose 1-epimerase) | 183,4 | 421,1 | 1172,7 | -2,3 | -6,4 |
| down | 209696_at | FBP1 | NM_000507 /// NM_001127628 | 2203 | fructose-1,6-bisphosphatase 1 | 245,7 | 1773,2 | 5663,1 | -7,2 | -23,1 |
| down | 201030_x_at | LDHB | NM_001174097 /// NM_002300 | 3945 | lactate dehydrogenase B | 8336,9 | 15165,64 | 18227,1 | -1,8 | -2,2 |
| down | 213564_x_at | LDHB | NM_001174097 /// NM_002300 | 3945 | lactate dehydrogenase B | 8230,7 | 12896,34 | 15382,6 | -1,6 | -1,9 |
| down | 204705_x_at | ALDOB | NM_000035 | 229 | aldolase B, fructose-bisphosphate | 39,3 | 9185,37 | 16975,3 | -233,5 | -431,5 |
| down | 211357_s_at | ALDOB | NM_000035 | 229 | aldolase B, fructose-bisphosphate | 36,5 | 6757,29 | 12180,9 | -185,1 | -333,7 |
| down | 217238_s_at | ALDOB | NM_000035 | 229 | aldolase B, fructose-bisphosphate | 18,4 | 7765,3 | 19070,8 | -422,8 | -1038,3 |
| down | 204704_s_at | ALDOB | NM_000035 | 229 | aldolase B, fructose-bisphosphate | 9,4 | 484,3 | 2638,8 | -51,7 | -281,6 |

Figure 11 (Continued)

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Forward primer
```

```
<400> SEQUENCE: 1
agaaaatctg gcaccacacc                                          20

<210> SEQ ID NO 2
<211> LENGTH: 20
<212> TYPE: DNA
<213> ORGANISM: Artificial Sequence
<220> FEATURE:
<223> OTHER INFORMATION: Reverse primer

<400> SEQUENCE: 2
cagaggcgta cagggatagc                                          20

<210> SEQ ID NO 3
<211> LENGTH: 20
<212> TYPE: DNA
<213> ORGANISM: Artificial Sequence
<220> FEATURE:
<223> OTHER INFORMATION: Forward primer

<400> SEQUENCE: 3
agcagaatgg cattgtaccc                                          20

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
aaagtgaccc cagtgacagc                                          20

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
tttcattgca ctggatctcg                                          20

<210> SEQ ID NO 6
<211> LENGTH: 21
<212> TYPE: DNA
<213> ORGANISM: Artificial Sequence
<220> FEATURE:
<223> OTHER INFORMATION: Reverse primer

<400> SEQUENCE: 6
cgtctatttt ggattgtcgg c                                        21

<210> SEQ ID NO 7
<211> LENGTH: 20
<212> TYPE: DNA
<213> ORGANISM: Artificial Sequence
<220> FEATURE:
<223> OTHER INFORMATION: Forward primer

<400> SEQUENCE: 7
gacccccggc aagggcattc                                          20

<210> SEQ ID NO 8
<211> LENGTH: 20
```

```
<212> TYPE: DNA
<213> ORGANISM: Artificial Sequence
<220> FEATURE:
<223> OTHER INFORMATION: Reverse primer

<400> SEQUENCE: 8
tggtttcccc gtcggtccca                                          20

<210> SEQ ID NO 9
<211> LENGTH: 20
<212> TYPE: DNA
<213> ORGANISM: Artificial Sequence
<220> FEATURE:
<223> OTHER INFORMATION: Forward primer

<400> SEQUENCE: 9
cttcattgtg ggagcagaca                                          20

<210> SEQ ID NO 10
<211> LENGTH: 20
<212> TYPE: DNA
<213> ORGANISM: Artificial Sequence
<220> FEATURE:
<223> OTHER INFORMATION: Reverse primer

<400> SEQUENCE: 10
ttctccagag ctgggttgtt                                          20

<210> SEQ ID NO 11
<211> LENGTH: 20
<212> TYPE: DNA
<213> ORGANISM: Artificial Sequence
<220> FEATURE:
<223> OTHER INFORMATION: Forward primer

<400> SEQUENCE: 11
ggcggctttg tgatttgtat                                          20

<210> SEQ ID NO 12
<211> LENGTH: 20
<212> TYPE: DNA
<213> ORGANISM: Artificial Sequence
<220> FEATURE:
<223> OTHER INFORMATION: Reverse primer

<400> SEQUENCE: 12
acctgaatcg ggggataaac                                          20

<210> SEQ ID NO 13
<211> LENGTH: 20
<212> TYPE: DNA
<213> ORGANISM: Artificial Sequence
<220> FEATURE:
<223> OTHER INFORMATION: Forward primer

<400> SEQUENCE: 13
accacagtcc atgccatcac                                          20

<210> SEQ ID NO 14
<211> LENGTH: 20
<212> TYPE: DNA
<213> ORGANISM: Artificial Sequence
<220> FEATURE:
<223> OTHER INFORMATION: Reverse primer
```

```
<400> SEQUENCE: 14
tccaccaccc tgttgctgta                                               20

<210> SEQ ID NO 15
<211> LENGTH: 20
<212> TYPE: DNA
<213> ORGANISM: Artificial Sequence
<220> FEATURE:
<223> OTHER INFORMATION: Forward primer

<400> SEQUENCE: 15
gtcggcctct ttgttaatcg                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse primer

<400> SEQUENCE: 16
cacatacatg ggcacaaagc                                               20

<210> SEQ ID NO 17
<211> LENGTH: 20
<212> TYPE: DNA
<213> ORGANISM: Artificial Sequence
<220> FEATURE:
<223> OTHER INFORMATION: Forward primer

<400> SEQUENCE: 17
gactctgccc ccatcacggc                                               20

<210> SEQ ID NO 18
<211> LENGTH: 20
<212> TYPE: DNA
<213> ORGANISM: Artificial Sequence
<220> FEATURE:
<223> OTHER INFORMATION: Reverse primer

<400> SEQUENCE: 18
gccaccgcaa caggacggta                                               20

<210> SEQ ID NO 19
<211> LENGTH: 21
<212> TYPE: DNA
<213> ORGANISM: Artificial Sequence
<220> FEATURE:
<223> OTHER INFORMATION: Forward primer

<400> SEQUENCE: 19
ttgctgacct gaggaacgcc t                                             21

<210> SEQ ID NO 20
<211> LENGTH: 21
<212> TYPE: DNA
<213> ORGANISM: Artificial Sequence
<220> FEATURE:
<223> OTHER INFORMATION: Reverse primer

<400> SEQUENCE: 20
caggacccac caatacgggc g                                             21

<210> SEQ ID NO 21
<211> LENGTH: 21
```

```
<212> TYPE: DNA
<213> ORGANISM: Artificial Sequence
<220> FEATURE:
<223> OTHER INFORMATION: Forward primer

<400> SEQUENCE: 21
agagcgggag ggcagctttc t                                           21

<210> SEQ ID NO 22
<211> LENGTH: 21
<212> TYPE: DNA
<213> ORGANISM: Artificial Sequence
<220> FEATURE:
<223> OTHER INFORMATION: Reverse primer

<400> SEQUENCE: 22
gggcaagctc atccgccaag t                                           21
```

COMPOUNDS FOR USE IN POLYCYSTIC KIDNEY DISEASE

This application is a National Stage Application of PCT/EP2013/064036, filed 3 Jul. 2013, which claims benefit of Ser. No. 61/667,615, filed 3 Jul. 2012 in the United States and which applications are incorporated herein by reference. To the extent appropriate, a claim of priority is made to each of the above disclosed applications.

BACKGROUND OF THE INVENTION

Polycystic kidney disease (PKD or PCKD, also known as polycystic kidney syndrome) is a cystic genetic disorder of the kidneys. There are two types of PKD: autosomal dominant polycystic kidney disease (ADPKD) and the less-common autosomal recessive polycystic kidney disease (ARPKD). PKD is caused by loss-of-function mutations in either PKD1 or PKD2.

In addition, there are a number of monogenic disorders characterized by renal cyst formation, including nephronophthisis (NPHP) affecting childrens and adolescents, Oral Facial Digital Syndrome (OFD1), Bardet Biedle Syndrome (BBS) among others, which manifest with renal cyst formation. These diseases are collectively called the "ciliopathies". These are syndromic forms which manifest in several different organs and, when involving the kidney, invariably present with cysts. Although the individual genes mutated in these diseases are different, it is believed that the molecular basis of cyst formation are shared by all diseases, as pointed out by the fact that all of the proteins encoded by said mutated genes contribute to the correct functioning of the primary cilium.

SUMMARY OF THE INVENTION

ADPKD is the most common of all the hereditary cystic kidney diseases with an incidence of 1 to 2:1,000 live births.

Cysts originate from any segment of the renal tubule in only 5-10% of the nephrons, a condition that should be compatible with a normal renal function. However, the gradual expansion of cysts compresses and eventually replaces the normal tissue, causing end-stage renal disease in a majority of patients. Thus, therapeutic interventions targeting cyst expansion is currently being tested in multiple clinical trials to delay renal disease progression.

Polycystic Liver Disease (PLD) usually describes the presence of multiple cysts scattered throughout normal liver tissue, in association with polycystic kidney disease. Polycystic Liver Disease can also present as an independent genetic disease, called Autosomal Dominant Polycystic Liver Disease (ADPLD) due to mutations in different genes. A recent study has however demonstrated that the mechanism of renal cyst formation in this diseases falls back to a decreased activity of the Pkd1 gene, showing that the mechanism of cyst formation in ADPLD might be identical to that of ADPKD (Fedeles et al, Nat Gen 43:639-47, 2011).

Finally, additional manifestations of ADPKD include: pancreatic cyst, cardiovascular abnormalities (aortic and intracranial aneurisms) and epididimal cyst formation in the testis associated with male infertility.

DETAILED DESCRIPTION

Figures Legend

FIG. 1: Metabonomics revealed increased glycolysis in Pkd1$^{-/-}$ MEFs a. Pkd1$^{-/-}$ cells (white column) have increased ATP content compared to the Pkd1$^{+/+}$ cells (black column) (11.21+/−0.41 and 5.59+/−0.94 pmoles per 250 ng of proteins, respectively, at 48 h; P=0.0007 by Analysis of variance followed by t-test). b. Overlay of $^1$H NMR spectra of the extracellular medium alone (control) or incubated in the presence of Pkd1$^{+/+}$ or Pkd1$^{-/-}$ cells for 24 h, expansion of the spectral regions corresponding to glucose and lactate resonances are shown. c. Quantitative analysis of NMR spectra revealed decreased glucose and increased lactate concentration in Pkd1$^{-/-}$ as compared to Pkd1$^{+/+}$ cells (control medium: 30.85+/−0.32 mM*10$^{-6}$ cells; Pkd1$^{+/+}$: 13.54+/−0.20 mM*10$^{-6}$ cells; Pkd1$^{-/-}$:6.27+/−0.08 mM*10$^{-6}$ cells; P=0.0008 by t-test) and increased lactate concentration in Pkd1$^{-/-}$ as compared to Pkd1$^{+/+}$ cells (12.56+/−0.25 and 5.31+/−0.10 mM, respectively. 10$^{-6}$ cells; P=0.0004 by t-test). d. Quantification of lactate production using a commercial assay (EnzyChrom™ L-lactate Assay) confirmed increased production in Pkd1$^{-/-}$ cells (37.87+/−9.14 nmoles.min$^{-1}$/10$^6$ cells) as compared to Pkd1$^{+/+}$ (8.17+/−2.62 nmoles.min$^{-1}$/10$^6$ cells) (P=0.0057 by t-test). A similar increase was observed in Pkd1 conditional mutant cells treated in the presence of a Cre recombinase (29.25+/−4.47 nmoles.min$^{-1}$/10$^6$ cells) as compared to control cells non treated with Cre (11.28+/−0.91 nmoles.min$^{-1}$/10$^6$ cells) (t-test, P=0.0133). e. No difference in ATP content could be observed in Pkd1$^{+/+}$ cells compared to Pkd1 cells after 48 h of glucose starvation (respectively 39660+/−4619 and 53932+/−9402 RLU; Anova analysis followed by t-test, P=0.0777). f-g. The mitochondrial membrane potential measured with the fluorescent dye TMRM before and after treatment with FCCP (uncoupling the membrane potential). Fluorescence was assessed by time lapse microscopy (Pkd1$^{+/+}$:7.61+/−2.09 arbitrary units (a.u.); Pkd1$^{-/-}$: 6.88+/−0.54 a.u.; t-test gave P=0.5910) (f) or FACS analysis (Pkd1$^{+/+}$: 2.16+/−0.33 a.u.; Pkd1$^{-/-}$: 1.95+/−0.06 a. u.; t-test gave P=0.3626) (g). (h). Pkd1$^{+/+}$ and Pkd1$^{-/-}$ MEFs were treated in the presence of oligomycin (inhibiting the F1 ATP synthase) for 5 h. This caused the expected drop in ATP content for Pkd1$^{+/+}$ cells (from 102891+/−1042 to 38908+/−17139 RLU after Anova, t-test gave P=0.0030), while Pkd1$^{-/-}$ cells only displayed a slight decrease (from 147421+/−31458 to 127127+/−19028 RLU, after Anova t-test gave P=0.3932).

ns: P≥0.05; *: P<0.05; : P<0.01; *: P<0.001; Means+/−SD are shown. Data are representative of three independent experiments performed in triplicate. In f the average value of all three experiments is provided. Bar=10 μm.

Figure 2:
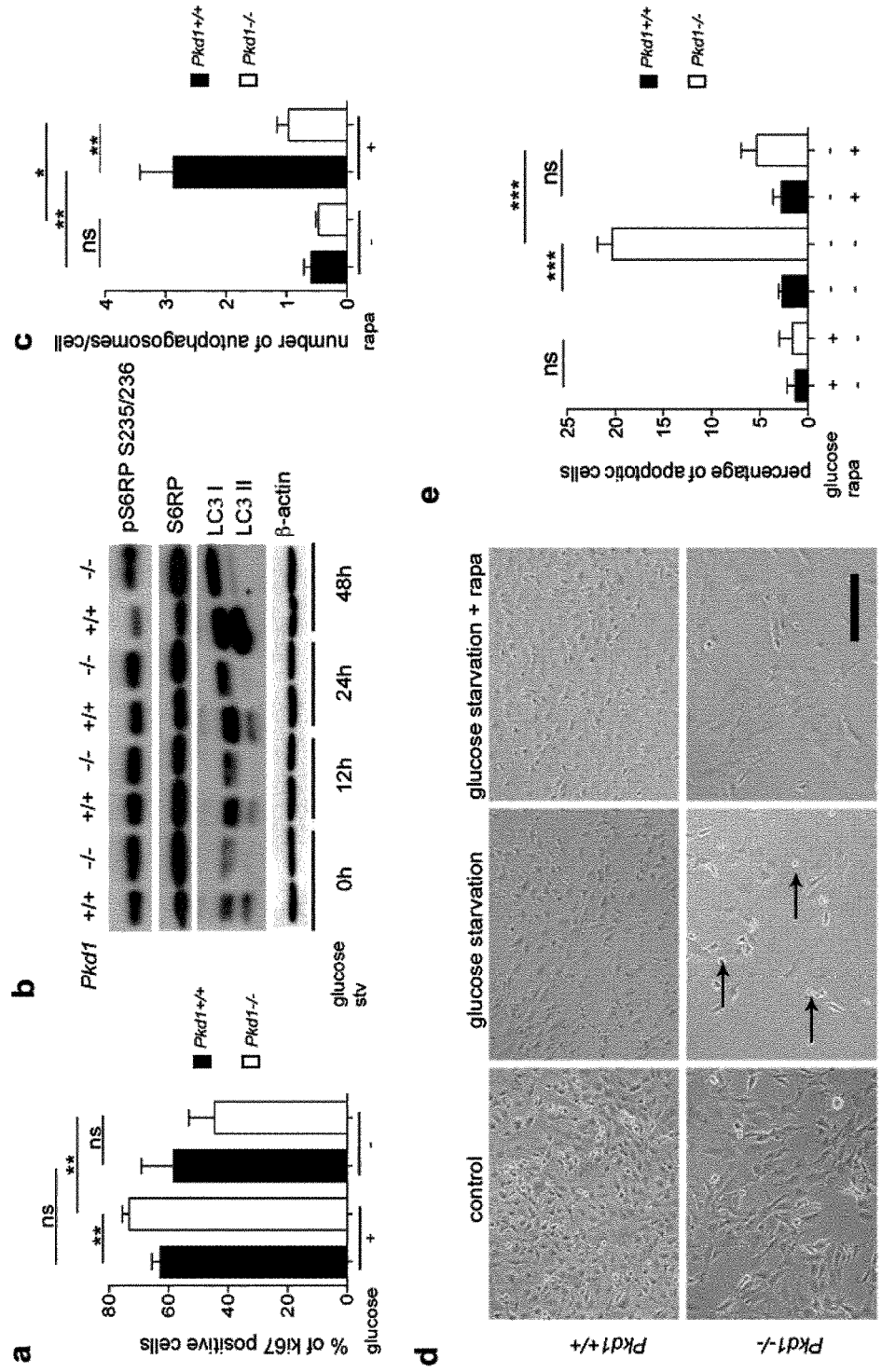
Figure 8:
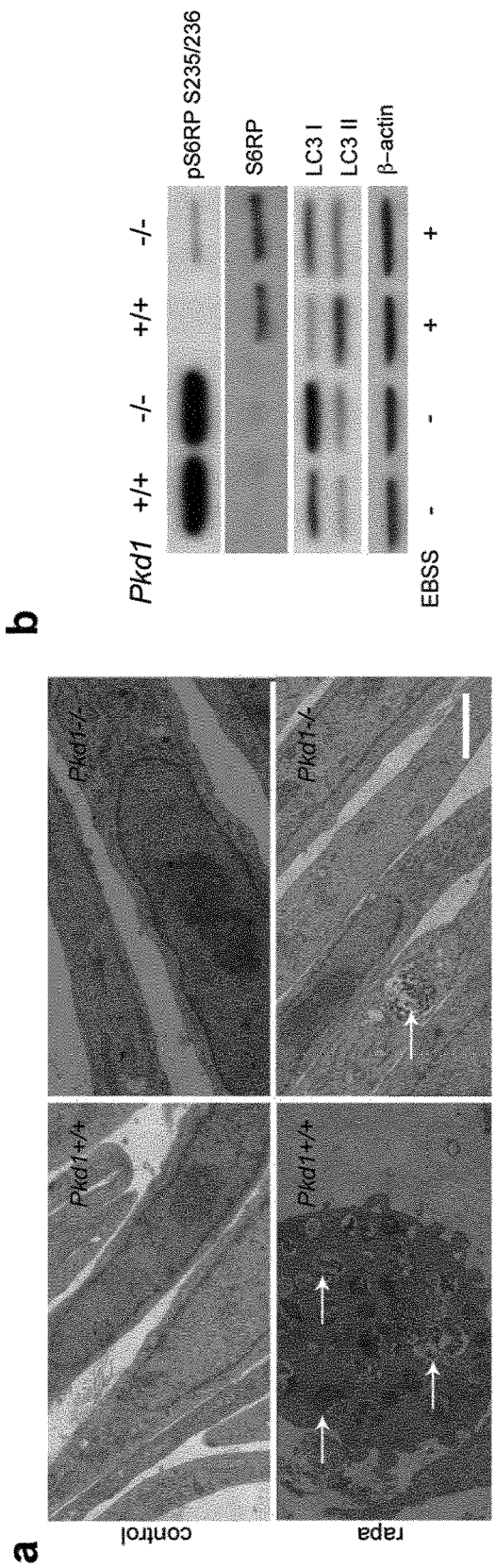

FIG. 2: Glucose addiction of Pkd1$^{-/-}$ cells and defect in autophagy a. Proliferation was measured as percentage of cells positive for staining of Ki67 over total cells. Pkd1$^{-/-}$ cells are more proliferative in the presence of glucose (Pkd1$^{+/+}$: 62.73+/−2.92 versus Pkd1$^{-/-}$: 73.28+/−2.27%; Anova, followed byt-test, P=0.0079), but their rate dropped dramatically after glucose starvation (Pkd1$^{+/+}$: 58.31+/−10.86 versus Pkd1$^{-/-}$: 44.65+/−8.57%; Anova followed by t-test, P=0.1624). b. Western-Blot for LC3-II revealed that glucose starvation for 12, 24 and 48 h induced high levels of LC3-II indicative of autophagy in Pkd1$^{+/+}$ but not in Pkd1$^{-/-}$ cells. c. Quantification of the number of autophagosomes per cells evaluated by EM (FIG. 8a) in the presence or absence of rapamycin treatment (50 nM) (after rapamycin treatment Pkd1$^{+/+}$: 2.87+/−0.55 versus Pkd1$^{-/-}$: 0.96+/−0.18 a.u.; Anova followed by t-test, P=0.0048). d. Cells were glucose-starved for 48 h and bright field images captured. Pkd1$^{-/-}$ cells suffered more than the Pkd1$^{+/+}$ with numerous visible dying cells (arrow). Treatment with rapamycin (20 nM) rescued this phenotype. e. Quantification of apoptosis using the TUNEL assay shows that after glucose starvation, Pkd1$^{-/-}$ cells underwent apoptosis (20.33+/−1.52%) significantly more than the Pkd1$^{+/+}$ cells (2.7+/−0.34%) (Anova followed by t-test, P<0.0001).

ns: not significant; *: P<0.05; : P<0.01; *: P<0.001; Means+/−are shown. Graphs are representative of at least three independent experiments performed in triplicate. Bar=200 μm.

Figure 3:
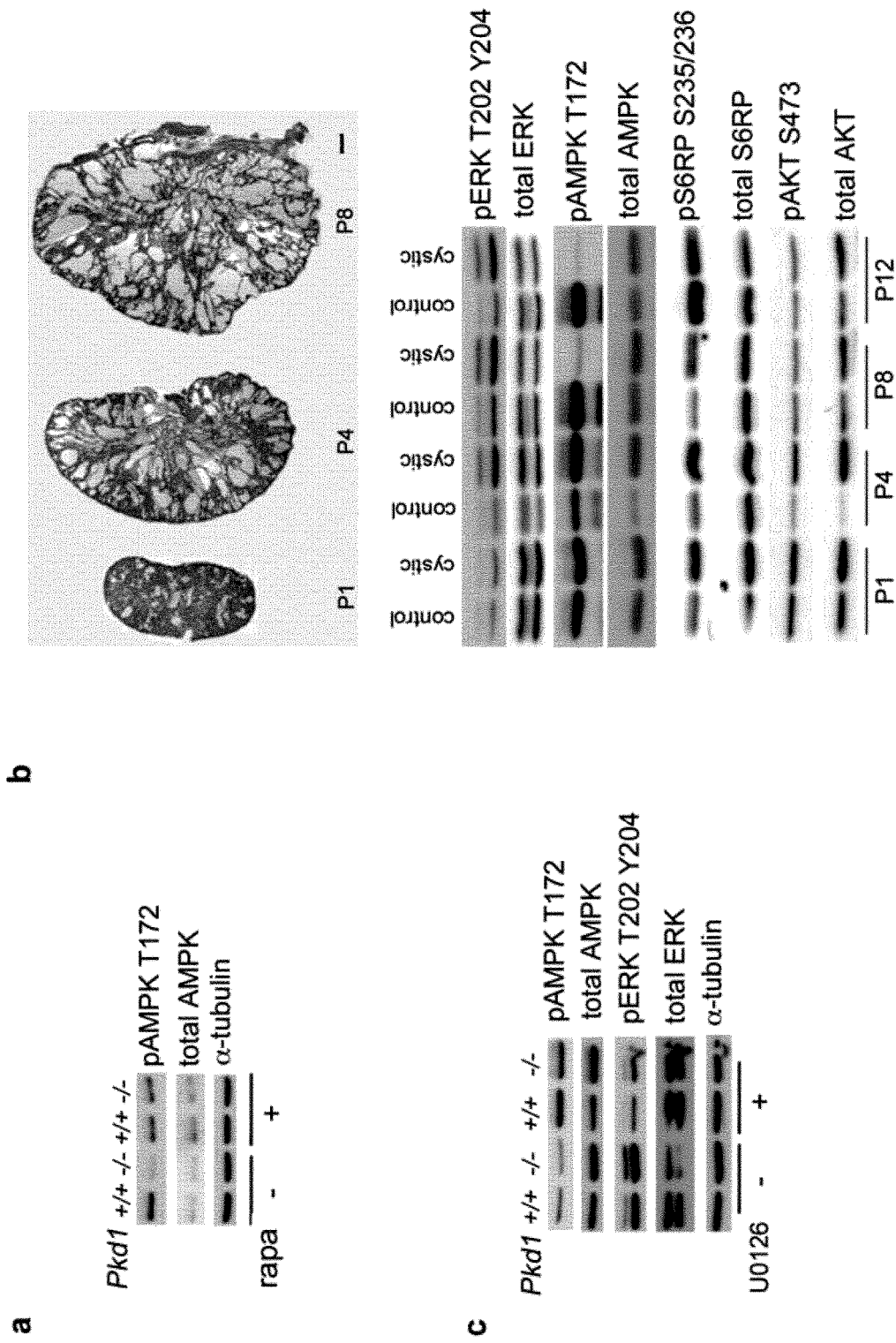
Figure 3:
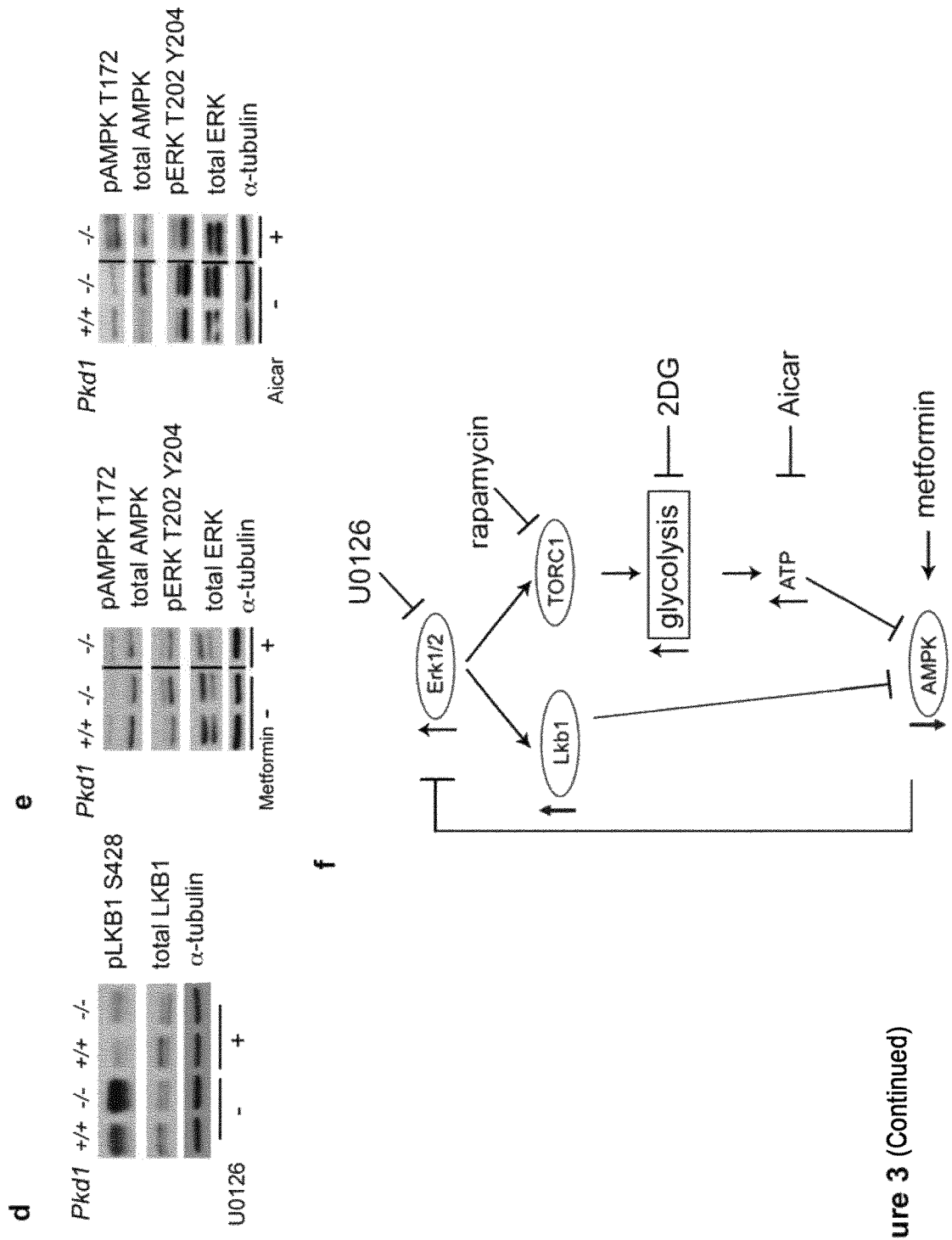

FIG. 3: AMPK and ERK crosstalk in vitro and in vivo a. pAMPK was downregulated in Pkd1$^{-/-}$ MEFs cells as compared to Pkd1$^{+/+}$ in standard conditions (in high glucose medium). Treatment in the presence of rapamycin 20 nM for 4 h showed an increase of phosphorylation of pAMPK in Pkd1$^{-/-}$ cells. b. Representative images show the increase in size and cysts in Pkd1$^{-/flox}$:Ksp-cre kidneys at P1, P4 and P8. At P1, P4, P8 and P12 kidneys Pkd1$^{flox/-}$:Ksp-Cre mice were lysed and biochemically analyzed by western blot, revealing that pERK and pS6RP were up-regulated at P1 and P4 whereas AMPK was down-regulated at P8 and P12. pAkt levels (S473) do not appear to change. c. Treatment in the presence of 30 μM UO126 for 12 h restores normal pERK and pS6RP and enhances pAMPK, in Pkd1$^{-/-}$ MEFs cells. d. Western blot analysis of LKB1 phosphorylation at 5428 revealed an increased phosphorylation level in Pkd1$^{-/-}$ MEFs as compared to controls, while treatment with the ERKs inhibitor UO126 reduced pLKB1 levels in both Pkd1$^{+/+}$ Pkd1$^{-/-}$ MEFs. e. Treatment of Pkd1$^{-/-}$ MEFs in the presence of either metformin (2 mM) or AICAR (1 mM) showed that not only pAMPK levels are restored, as expected, but also pERK are restored to baseline levels. f. Schematic view of the molecular network likely acting in Pkd1 mutant cells and kidneys. ERKs act by enhancing mTOR activity which results in enhances glycolysis and diminished AMP levels on the one side, and it acts on LKB1-AMPK directly on the other.

Results are representative of experiments performed a minimum of three times.

Figure 4:
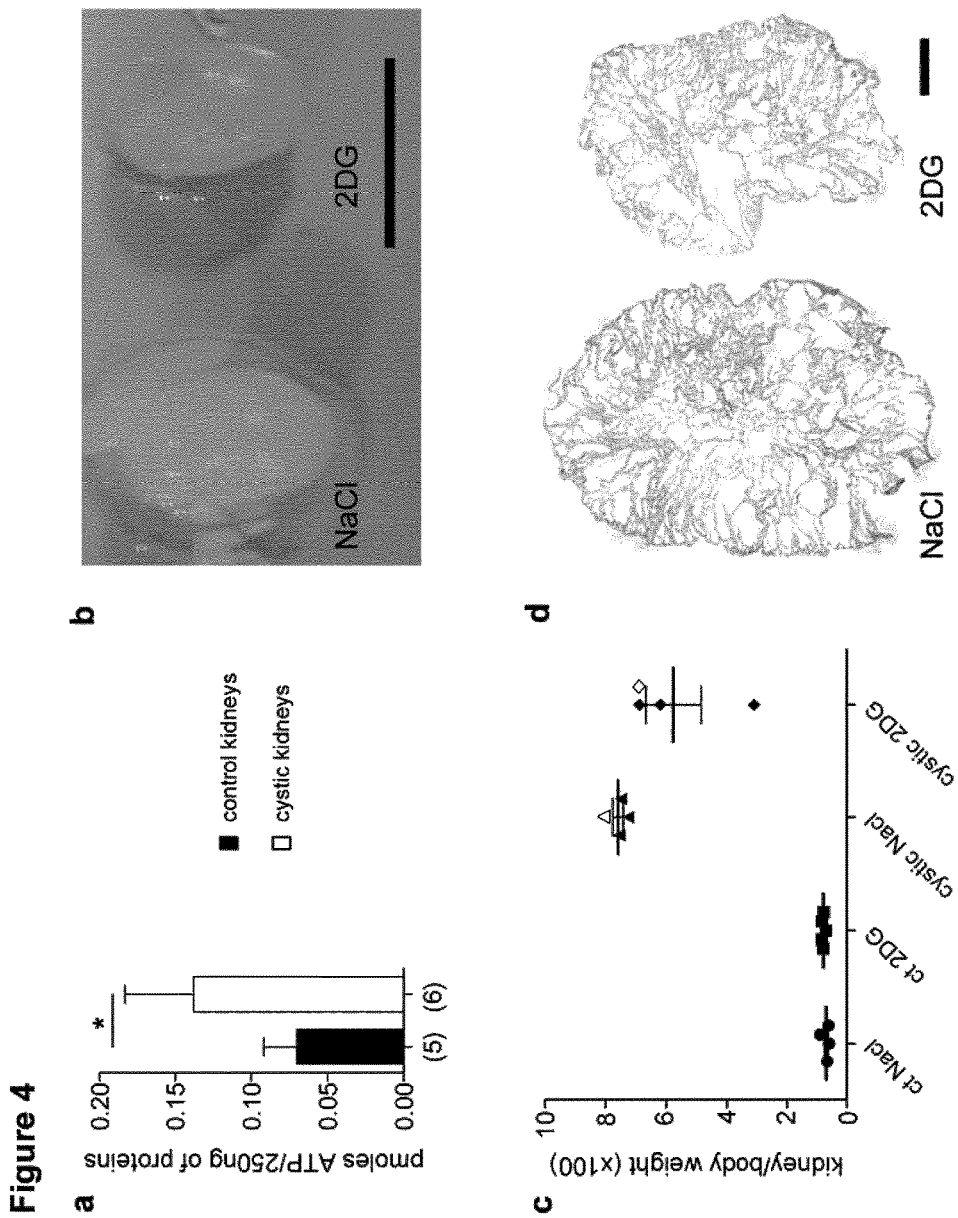
Figure 4:
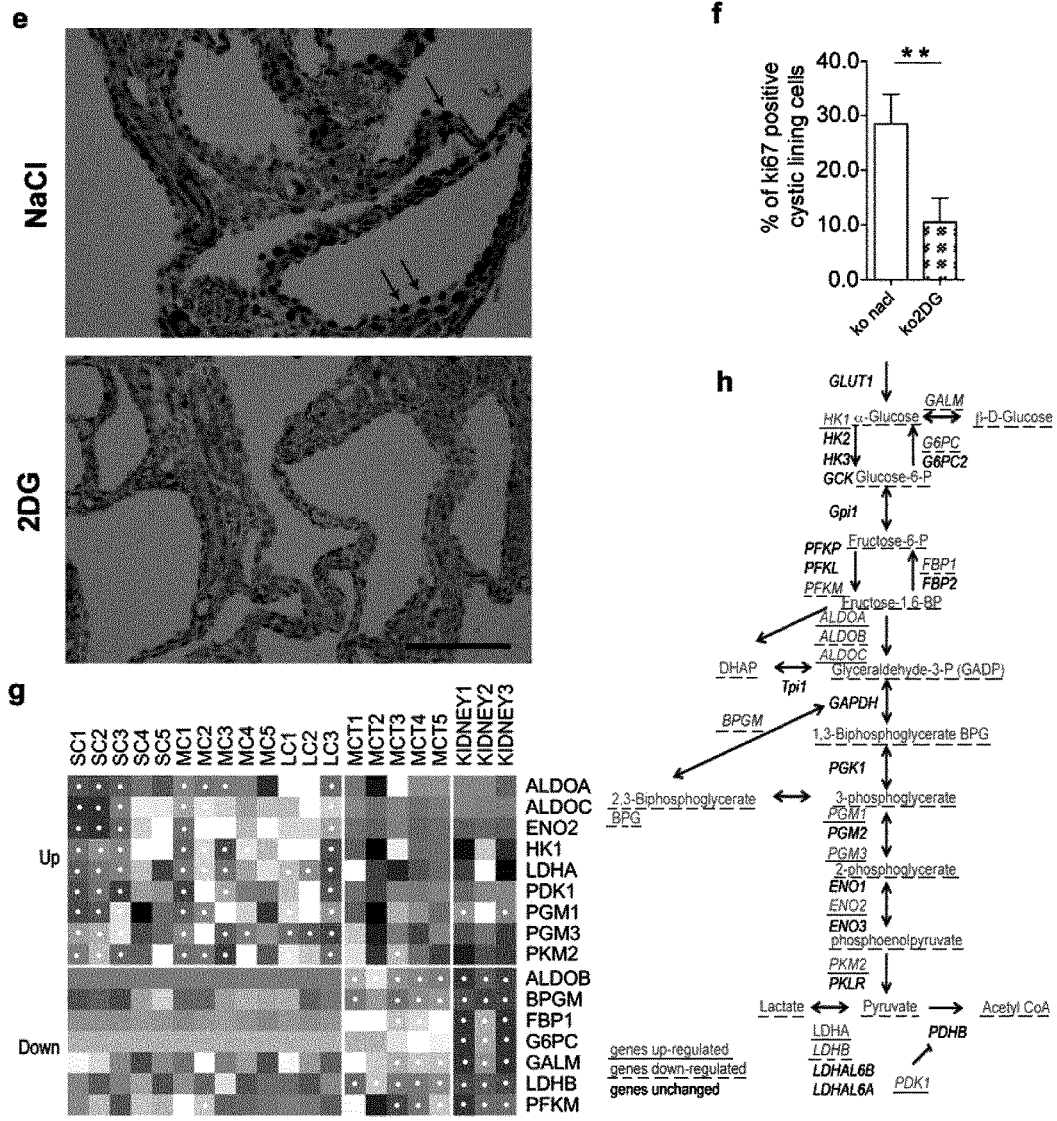

FIG. 4: Increased transcription of the glycolytic network in ADPKD patients and effect of 2DG on proliferation a. Pkd1$^{-/flox}$:ksp-cre kidneys exhibited an enhanced ATP content compared to the control kidneys at P4 (control: 0.07+/−0.02 versus cystic 0.13+/−0.04 pmoles of ATP/250 ng of proteins; t-test, P=0.0140). b. Representative example of the gross appearance of the cystic Pkd1$^{-/flox}$:ksp-cre kidneys of mice at P8 treated daily (from P6 to P8) at 500 mg/kg with 2DG or with vehicle (NaCl). c. Ratio of renal weight over body weight showing an effect of the treatment with the 2DG only on mutant animals. d. Histology of the kidneys from littermate mice treated with 2DG or vehicle (sections of the kidneys belonging to the mice shown as empty dots in the histogram in c). e. Ki67 assay showing decreased proliferation index in the cystic kidneys of Pkd1$^{-/flox}$:ksp-cre mice treated with 2DG compared to those treated with vehicle (NaCl). f. Quantification of the proliferation rates in the cyst lining epithelium from mice treated as in e (Nacl: 28.48+/−5.39% and 2DG 10.53+/−4.38%; t-test, P.0021). g Panels showing the hitmap of genes coding for glycolytic and glucogenesis enzymes differentially expressed between the cysts and MCT samples as described. Up-regulated genes are shown in the box with a dot, and down-regulated genes in the other ones. SC, small cysts; MC, medium cysts; LC, large cysts; MCT, minimally cystic tissue; KIDNEY, normal renal cortical tissue. h. The scheme shows the glycolytic cascade, the genes up-regulated in cystic kidneys from ADPKD patients compared to the normal kidneys are underlined, the ones down-regulated are underlined with a dotted line and the ones unchanged are not underlined. *: P<0.05; **: P<0.01; Means+/−SD are provided. b to e show the results generated in one litter. Experiments were repeated on three independent litters. Bars is 10 mm in b, 1 mm in d and 100 μM in e.

Figure 5:
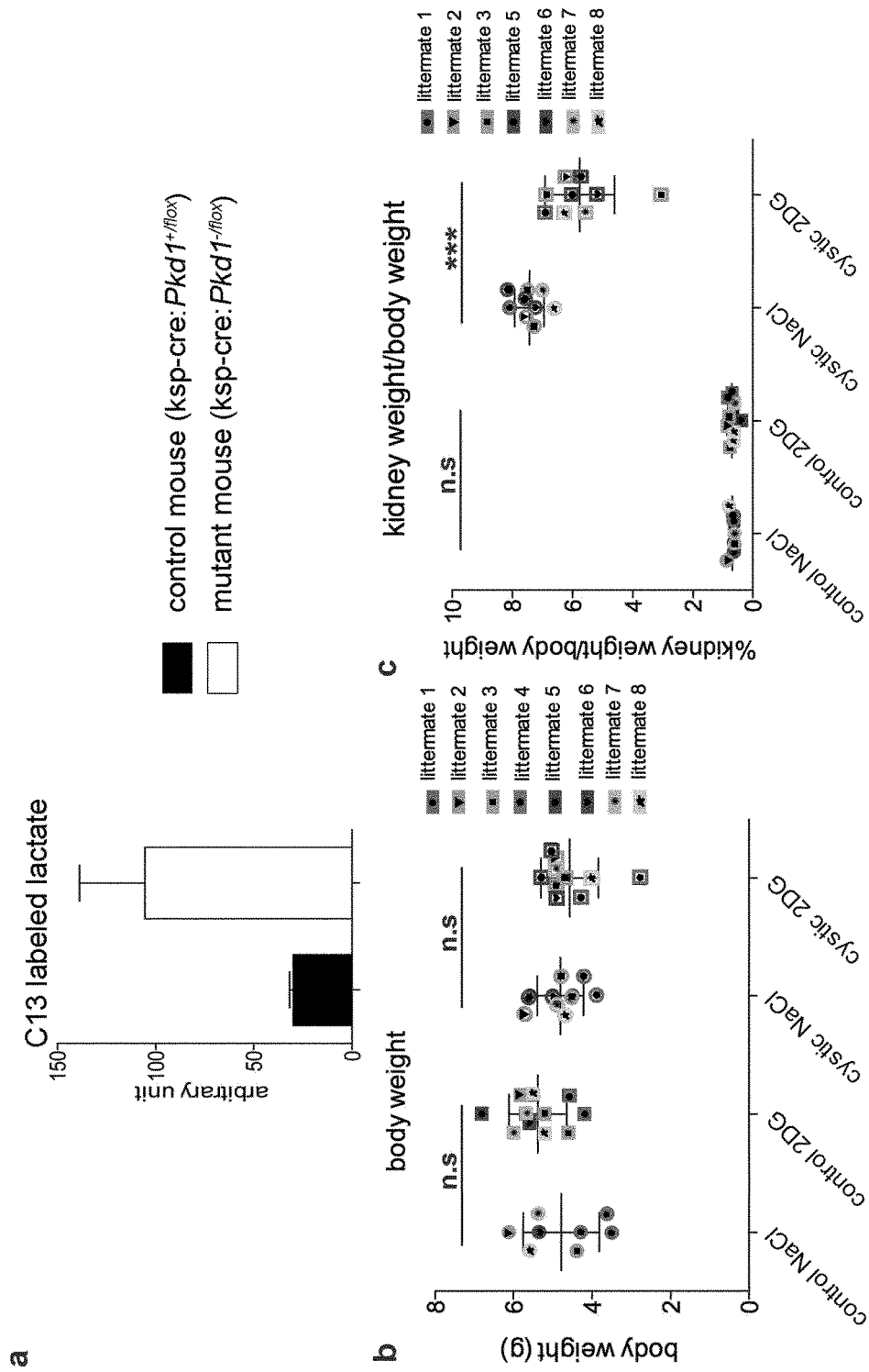
Figure 5:
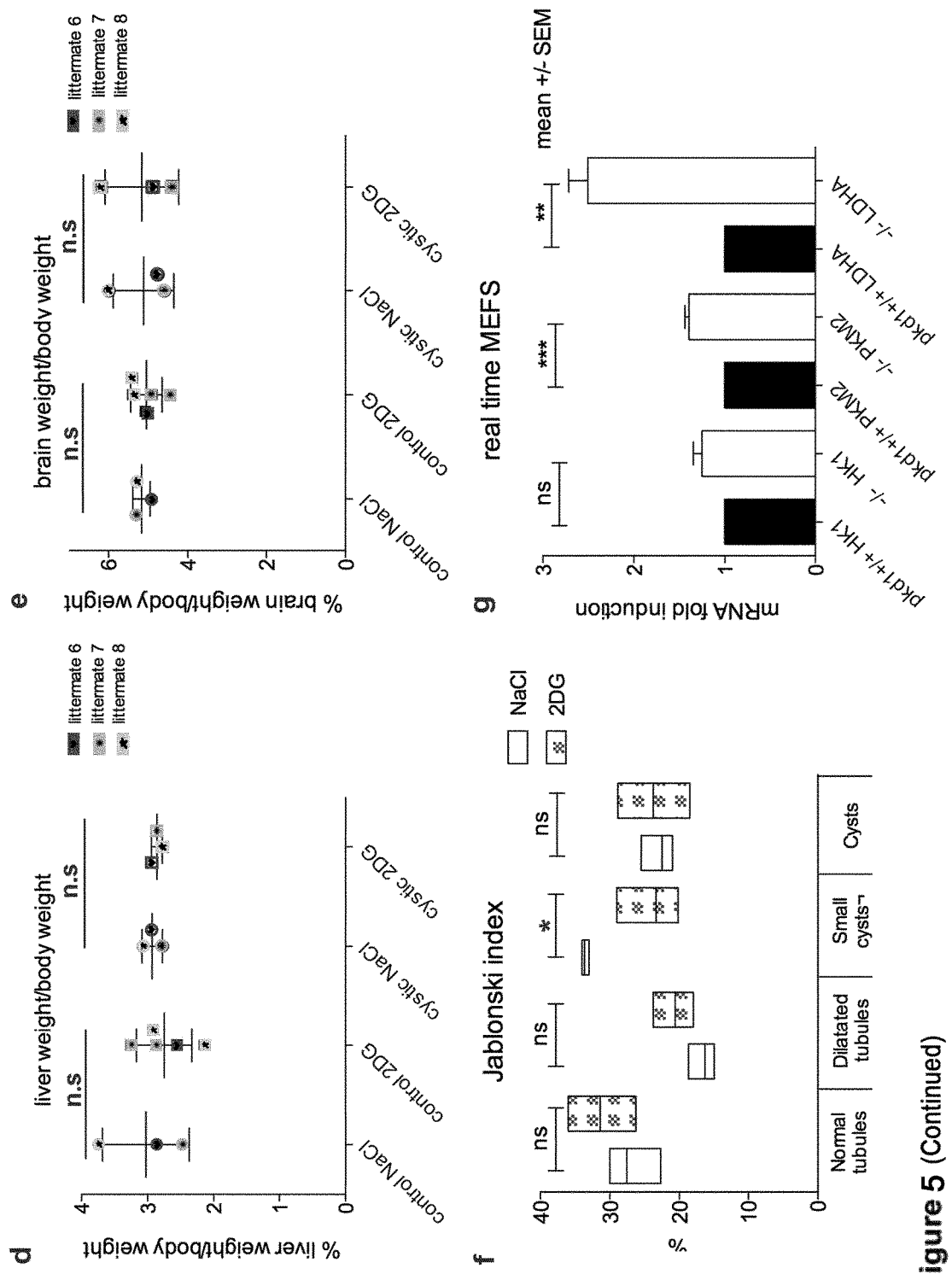

FIG. 5: In vivo glycolytic flow in mutant kidney and effect of 2DG a. In vivo glycolytic flow is increased in mutant kidney. We used C13 labeled glucose to follow the glycolytic flow in vivo. Labeled glucose was injected intracutaneously at P8 in a wt (ksp-cre: Pkd1$^{+/flox}$) and a mutant mouse (ksp-cre: Pkd1$^{-/flox}$) and after 40 min the mouse was sacrificed and C13 labeled lactate was measured in the kidney by NMR. The C13 labeled lactate contained in the kidneys corresponding to the area under the peaks normalized by the dry weight is higher in cystic compared to the control kidneys. Mean of the two kidneys of one mouse; SD are indicated. b. 2DG treatment does not alter the global physiology. wt mice (ksp-cre: Pkd1$^{+/flox}$) or mice with cystic kidneys (ksp-cre: Pkd1$^{-/flox}$) were treated daily with 2DG at 500 mg/kg or vehicle from P6 to P8. To investigate if the treatment altered the whole metabolism we used the body weight as a read out. 2DG treatment did not alter the body weight from mutant mice (ksp-cre: Pkd1$^{-/flox}$) or wt mice (ksp-cre: Pkd1$^{+/flox}$); ns: P≥0.05. c. 2DG treatment does reduce the ratio of kidney weight on body weight solely in mutant mice. 2DG treatment from P6 to P8 significantly reduced the weight of the treated cystic kidneys normalized by the body weight compared to the non treated ones, whereas 2DG did not affect the kidney weight in the wt mice; ns: P≥0.05; ***P<0.001. d-e. 2DG treatment does not alter the ratio of liver and brain weight on body weight. In contrast to the kidneys, other organs weight like livers (d) and brains (e) normalized by body weight did not showed effect of 2DG. Confirming that the 2DG treatment did not alter the normal physiology of the mouse but is specific of the cystic kidneys. ns: P≥0.05. f. 2DG treatment of cystic kidneys increases the number of normal tubules and decreases the number of cysts. The cystic index of mutant kidneys treated with 2DG or vehicle was determined using the Jablonski index method which is based on the measure of the area of lumen of the tubules. Treatment with 2DG slightly reduced the number of normal and dilated tubules in the treated kidneys compared to the untreated ones and significantly reduced the number of small cysts. g. Genes coding for glycolytic enzymes are more expressed in Pkd1$^{-/-}$ MEFs. To check for the up-regulation of glycolysis, real time analysis of the key glycolytic enzymes HK1, PKM2 and LDHA was performed in Pkd1$^{+/+}$ and Pkd$^{-/-}$ MEFs. The results showed a slight increase of HK1 expression and significant increase of PKM2 and LDHA expression in Pkd1$^{-/-}$ compared to the Pkd1$^{+/+}$ MEFs.

Figure 6:
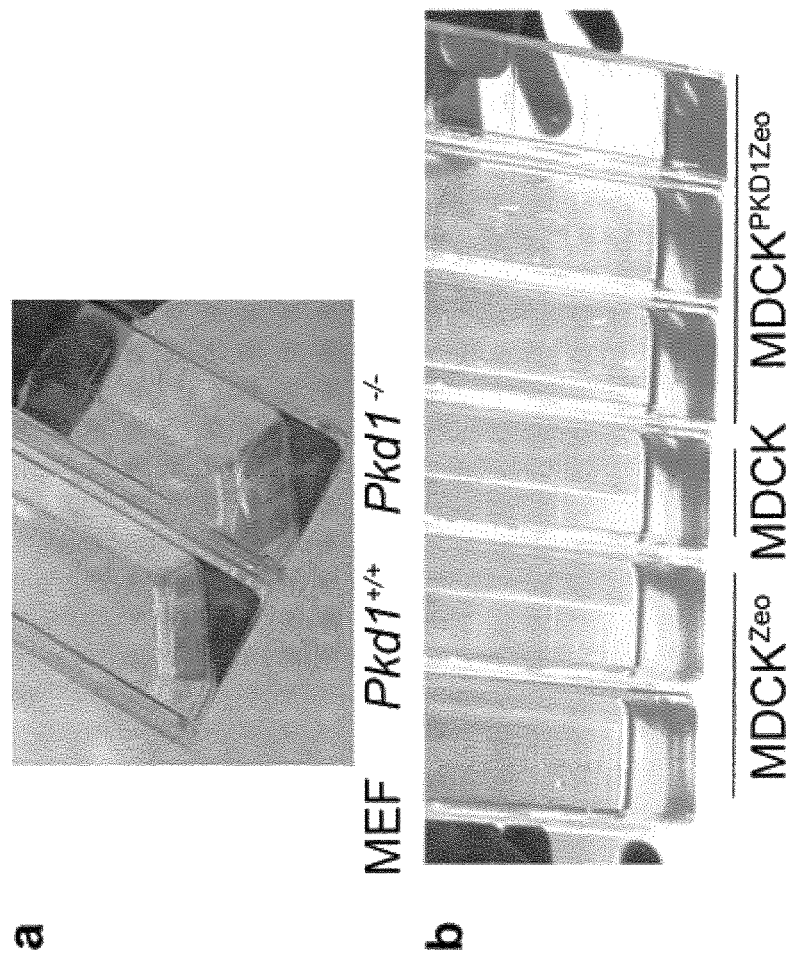

FIG. 6: Pkd1 absence correlates with a more acid culture medium a. The culture medium from Pkd1$^{-/-}$ MEF was more acid than Pkd1$^{+/+}$ MEF. b. The culture medium is less acid (darker) in PC-1 over expressing MDCK cells compared to control cells.

Figure 7:
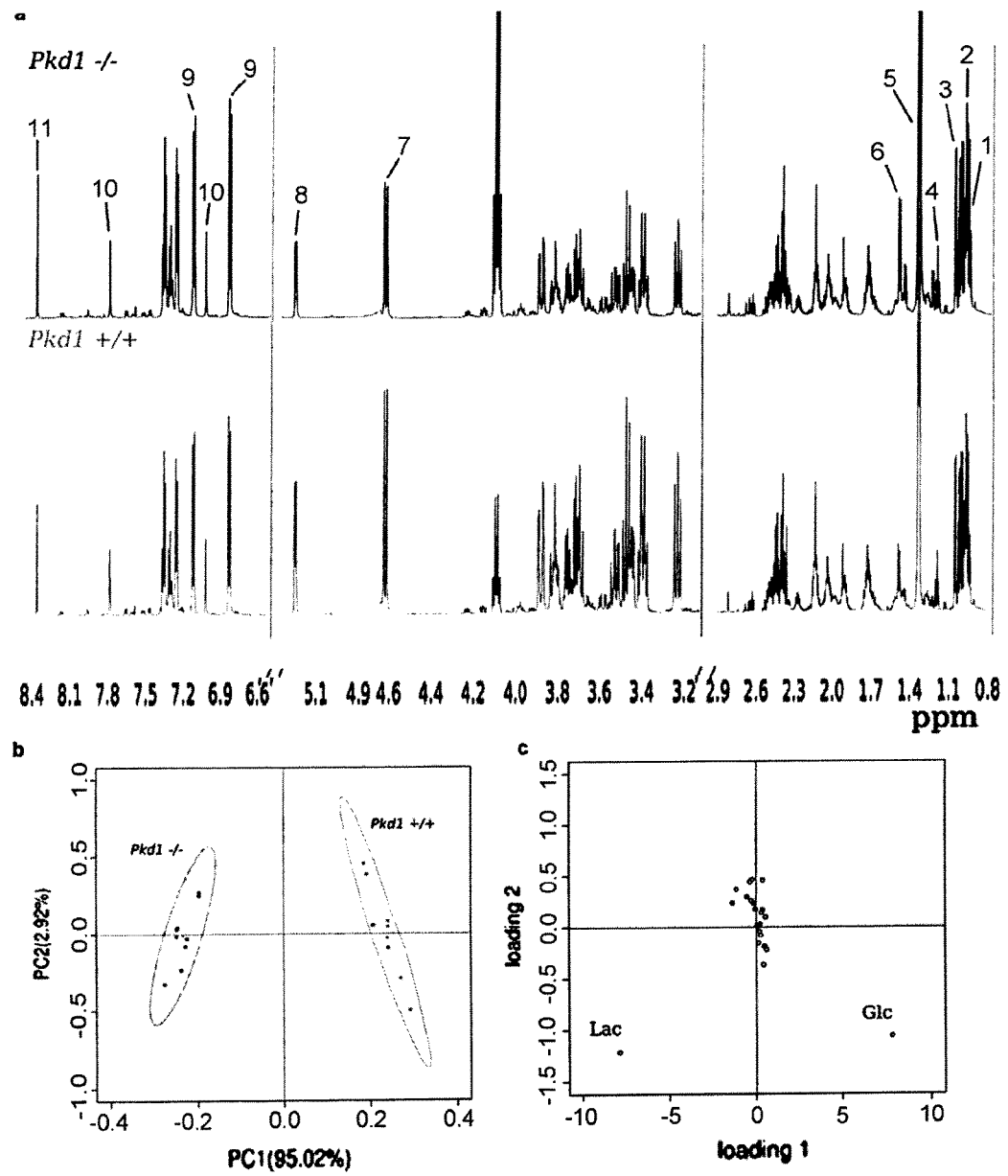

FIG. 7: Metabolic profiling of the extracellular medium conditioned with Pkd1$^{-/-}$ and Pkd1$^{+/+}$ MEFs a. Representative 1D-1HCPMG NMR spectra of Pkd1$^{-/-}$ and Pkd1$^{+/+}$ MEFs conditioned medium with assignments: 1=leucine; 2=valine; 3=isoleucine; 4=ethanol; 5=lactate; 6=alanine; 7=b-glucose; 8=a-glucose; 9=tyrosine; 10=histidine; 11=formic acid. Assignment details are listed in Supplementary Table 1. b. Principal component analysis (PCA) score plot and c. loading plot. PCA allows to cluster the spectra into medium conditioned with Pkd1$^{-/-}$ MEFs (dark gray) and with Pkd1$^{+/+}$ MEF (light gray) Ellipsoids around groups correspond to the 95% confidence interval. The loading plot of the first and the second principal component (PC1 and PC2) indicates that glucose and lactate are the main metabolites distinguishing the exometabolome of Pkd1$^{-/-}$ MEFs from the one of Pkd1$^{+/+}$ MEFs.

FIG. 8:

a. Electron microscopy images show autophagosomes in Pkd1$^{+/+}$ and Pkd1$^{-/-}$ MEF cells treated in the presence or absence of rapamycin 50 nM. b. Pkd1$^{+/+}$ and Pkd1$^{-/-}$ MEF were cultured in the presence of EBSS for 3 hrs followed by western blot analysis using anti-LC3 antibodies, revealing defective autophagy in Pkd1$^{-/-}$ cells.

FIG. 9:

a,b. Real time analysis of glycolytic gene expression in serum starvation with and without rapamycin 20 nM in (a) Pkd1$^{+/+}$, Pkd1$^{-/-}$ (b) Tsc2$^{+/+}$ and Tsc2$^{-/-}$ MEFs cells. c. The increased acidification of medium of MEFs cells Pkd1$^{-/-}$ was restored by treatment with rapamycin 50 nM for 48 h. Bar represents 2 μm.

FIG. 10: Quantification of the metabolites in the extra-cellular medium from Pkd1$^{+/+}$ and Pkd1$^{-/-}$ MEFs FIG. 11: Glycolytic gene expression in cystic compared to normal kidneys List of the genes coding for glycolytic enzymes and their score in small cysts, medium cysts and large cyst, minimally cystic tissue and normal kidney tissue.

To study alterations caused by defective PKD1 function we isolated Mouse Embryonic Fibroblasts (MEFs) from Pkd1$^{+/+}$ or Pkd1$^{-/-}$ mice [Distefano, G. et al. Polycystin-1 regulates extracellular signal-regulated kinase-dependent phosphorylation of tuberin to control cell size through mTOR and its downstream effectors S6K and 4EBP1. *Mol Cell Biol* 29, 2359-71 (2009)], and using these cells we serendipitously identified a novel pathogenic process. During routine culture, we noticed that Pkd1$^{-/-}$ cells acidified the medium faster than the Pkd1$^{+/+}$ while the opposite was observed in cells over-expressing PKD1 (FIG. 6). This observation was also replicated in growth-arrested cells (100% density) suggesting an intrinsic, proliferation-independent metabolic increase in Pkd1$^{-/-}$ cells. Indeed, Pkd1$^{-/-}$ cells had much higher ATP content as compared to Pkd1$^{+/+}$ (FIG. 1a). To determine which metabolic pathways were altered in these cells, we performed a metabolomic profiling of the conditioned extracellular medium of Pkd1$^{+/+}$ and Pkd1$^{-/-}$ cells using NMR spectroscopy. An unsupervised statistical analysis revealed that the metabolomic profile of Pkd1$^{-/-}$ cells differs significantly from that of Pkd1$^{+/+}$ cells (FIG. 7 and FIG. 10), the most prominent alteration being reduced glucose and increased lactate concentrations (FIGS. 1b and c and FIG. 7). These data suggest that Pkd1$^{-/-}$ cells use glycolysis as a source of energy. Indeed, glucose deprivation completely abrogated the increased ATP content of Pkd1$^{-/-}$ cells (FIG. 1e). Since glucose metabolism is also the main source of energy through oxidative phosphorylation occurring in the mitochondria, we analyzed the mitochondrial membrane potential in Pkd1$^{+/+}$ and Pkd1 cells using two independent quantification techniques (FIGS. 1f and 1g). No significant difference could be appreciated between the two cell lines (FIGS. 1f and 1g). In line with this, treatment with oligomycin, a potent inhibitor of the mitochondrial ATP-synthase, decreased the ATP content in both cell lines, as expected, but did not restore the difference between Pkd1$^{+/+}$ and Pkd1$^{-/-}$ cells (FIG. 1h). These data suggest that an alternative metabolic pathway that is glucose-dependent is the source of the differential ATP content between the two cell lines. We conclude that Pkd1$^{-/-}$ cells preferentially use glycolysis, in a process similar to the Warburg's effect observed in cancer [Chiaradonna, F. et al. From cancer metabolism to new biomarkers and drug targets. *Biotechnol Adv* 30, 30-51 (2012); Woo, D. Apoptosis and loss of renal tissue in polycystic kidney diseases. *N Engl J Med* 333, 18-25 (1995)].

Figure 9:
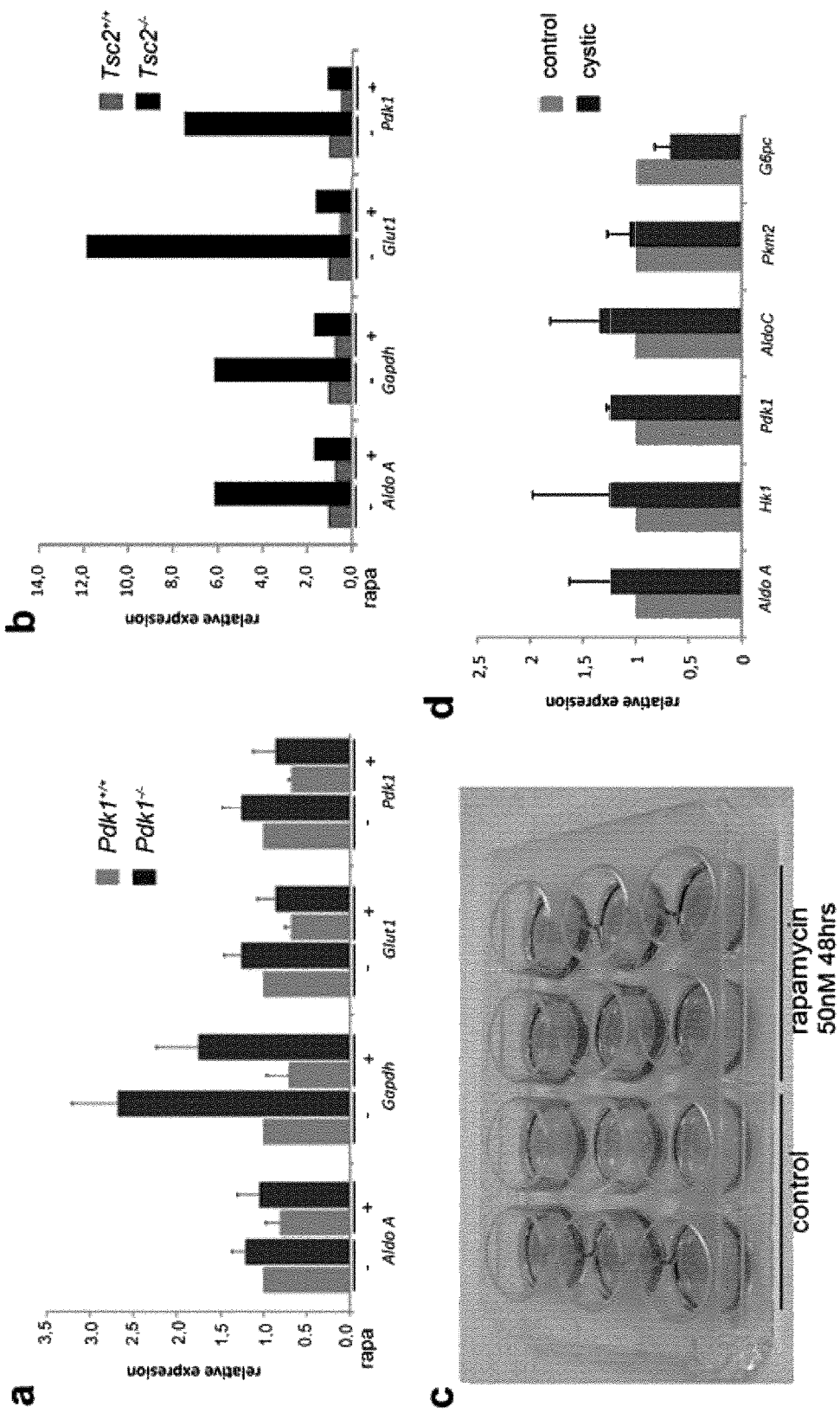

A defective balance between proliferation and apoptosis has been observed in ADPKD tissues and PKD1 mutant cells [Woo, D. cited]. We thus tested if increased glucose metabolism contributes to increased proliferation and/or apoptosis in these cells. Indeed, glucose deprivation restored the proliferation index of Pkd1$^{-/-}$ cells similar to that of Pkd1$^{+/+}$ cells (FIG. 2a). In addition, while the control cells deprived of glucose activated cell autophagy to survive, Pkd1$^{-/-}$ cells failed to activate the autophagic response (FIGS. 2b and 2c and FIG. 8) but instead displayed increased apoptotic rates (FIGS. 2d and e). Consistent with previous studies we also found that this effect is in part dependent on mTORC1 [Choo, A. Y. et al. Glucose addiction of TSC null cells is caused by failed mTORC1-dependent balancing of metabolic demand with supply. *Mol Cell* 38, 487-99 (2010) Duvel, K. et al. Activation of a metabolic gene regulatory network downstream of mTOR complex 1. *Mol Cell* 39, 171-83 (2010)]. Real-time PCR analysis revealed that Pkd1$^{-/-}$ cells displayed a transcriptional signature of glycolytic enzymes with a trend similar to that observed in Tsc1$^{-/-}$ cells and sensitive to rapamycin (FIG. 9 and FIG. 5g). Furthermore, treatment of Pkd1 mutant cells with rapamycin partially restored autophagy (FIG. 2c), cell survival under glucose deprivation (FIG. 2e), and down regulated metabolic rates (FIG. 9).

Consistent with the high ATP content we also found reduced levels of AMPK phosphorylation in Pkd1$^{-/-}$ cells as compared to Pkd1$^{+/+}$ (FIG. 3a). We found that the mice displayed cystic kidneys in KspCre: Pkd1$^{flox/-}$ mice displayed increased levels of pS6K1 and pERKs, no change in pAkt level, and decreased pAMPK level, although the last became more evident as the cystic kidneys expanded overtime (FIG. 3b).

We next tested if ERK inhibitors would reduce the glycolysis in Pkd1$^{-/-}$ cells. We found that inhibition of the ERK pathway reduced mTORC1 activation, lactate production and ATP content, and restored the levels of AMPK phosphorylation (FIG. 3c). Of interest, while restoration of glycolysis required long-term treatment with ERK inhibitors, the restoration of AMPK activity occurred much sooner, suggesting the involvement of an alternative pathway through which the ERKs could regulate AMPK. LKB1 was strongly phosphorylated at ERK-specific sites in Pkd1$^{-/-}$ cells compared to Pkd1$^{+/+}$ which was reverted by ERK inhibitors (FIG. 3d). Thus, we propose a dual role for ERK here: on the one side, they directly regulate LKB1 by inhibition of AMPK, on the other, they affect mTORC1 activity which in turn switches on glycolysis, increases ATP and further inhibits AMPK. Of great interest and unexpectedly, treatment of Pkd1$^{-/-}$ cells with metformin or AICAR (5-aminoimidazole-4-carboxamide ribonucleoside), both of which increased AMPK activity, also inhibited ERKs (FIG. 3e). These data suggest the existence of a negative feed-back loop whereby AMPK can regulate ERK activity. This pathway is regulated in a "circular manner" indicating that acting at any level of the cascade should restore the basal conditions (FIG. 3f).

Therapeutic interventions interfering with glucose metabolism in Pkd1 mutant cells/tissues thus present a novel strategy to retard cyst expansion. To confirm this, we used Ksp-Cre: Pkd1$^{flox/-}$ mice which develop early and severe PKD [Shibazaki, S. et al. Cyst formation and activation of the extracellular regulated kinase pathway after kidney specific inactivation of Pkd1. *Hum Mol Genet* 17, 1505-16 (2008)]. Compared to non-cystic controls, we found that the cystic kidneys displayed higher ATP levels (FIG. 4a), trend to transcriptional de-regulation of key glycolytic enzymes (FIG. 9), and increased generation of lactate specifically into the kidneys (FIG. 5a) suggesting that Pkd1 inactivation in the kidney results in a switch to glycolysis in vivo. Furthermore, treatment of these mice with a glucose analogue that cannot be metabolized (2-deoxyglucose, 2DG) reduced the kidney/body weight (FIGS. 4b and c and FIG. 5c) and cellular proliferation rates of the cystic kidneys (FIGS. 4e and 4f). Interestingly, the body weight of the mice (FIG. 5b) or the weight of other organs such as liver and brain do not change when 2DG is administered (FIGS. 5b, d and e). Finally, quantification of the cystic index of cystic kidneys treated in the presence of 2DG showed a significant decrease in the number of cysts (FIG. 5e) and an increased number of normal tubules (FIG. 5f).

This indicates that glucose analogues are useful as a novel form of therapy for ADPKD. This is only possible if the metabolic switch observed in vitro and in mice recapitulates a general feature of ADPKD in human. Thus, we examined the gene expression profile of both gluconeogenesis and glycolytic pathways using a previously established microarray database derived from PKD1 human renal cysts [Song, X. et al. Systems biology of autosomal dominant polycystic kidney disease (ADPKD): computational identification of gene expression pathways and integrated regulatory networks. *Hum Mol Genet* 18, 2328-43 (2009)]. We found that many enzymes involved in gluconeogenesis/glycolysis were differentially expressed in the renal cysts, with the vast majority of genes being down-regulated. Detailed analysis of this microarray database revealed that most of the genes encoding enzymes involved in gluconeogenesis were down-regulated genes while several genes encoding enzymes involved in glycolysis were up-regulated (FIGS. 4g and 4h and FIG. 11). Overall, these data indicate that increased glucose consumption and enhanced glycolysis are features of human ADPKD, thus confirming a therapeutic role for glycolysis inhibitor in ADPKD. The kidney is an organ with a great functional redundancy and loss of a small percentage of nephrons is not sufficient to cause its functional loss. As outlined above, renal failure in ADPKD is caused by the progressive renal cyst expansion affecting only a minority of nephrons. Therefore, the use of a molecule able to selectively kill the cells lining the cysts would most likely be an effective therapy.

Our study shows that the use of inhibitor of glycolysis is a valuable therapeutic approach to reduce proliferation and/or induce apoptosis selectively in the cystic epithelia. In a preferred embodiment, at least one glucose analogue is used, preferably selected from the group comprising 2DG, SB-204990, 3-bromopyruvate (3-BrPA), 3-BrOP, 5-thioglucose, mannose, galactose, gulose, a 2DG having a fluorine in place of a hydrogen at any position on the glucose ring, a 2DG having an amino group in place of a hydroxyl group at any position on the glucose ring other than the 6 position, 2-F-mannose, 2-mannosamine, 2-deoxygalactose, 2-F-deoxygalactose, and di, tri, and other oligosaccharides that contain one or more of the preceding 2DG analogs In a further embodiment, said glucose analogues are selected from the following group:

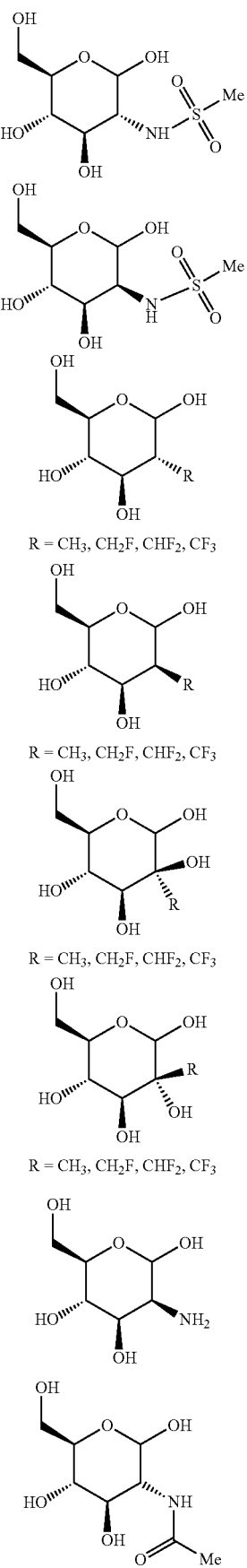

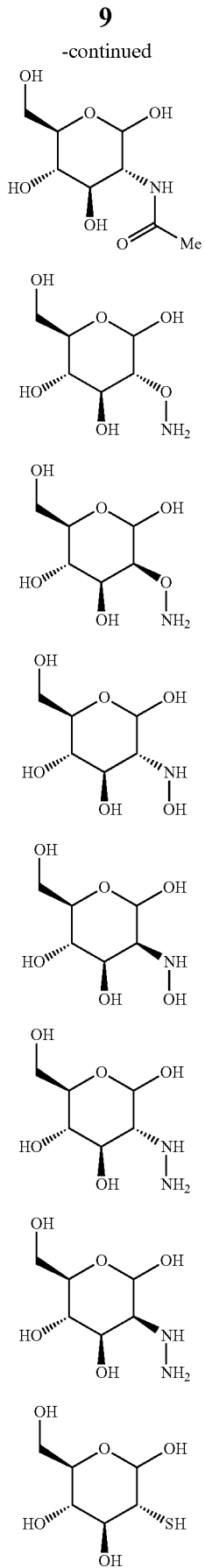

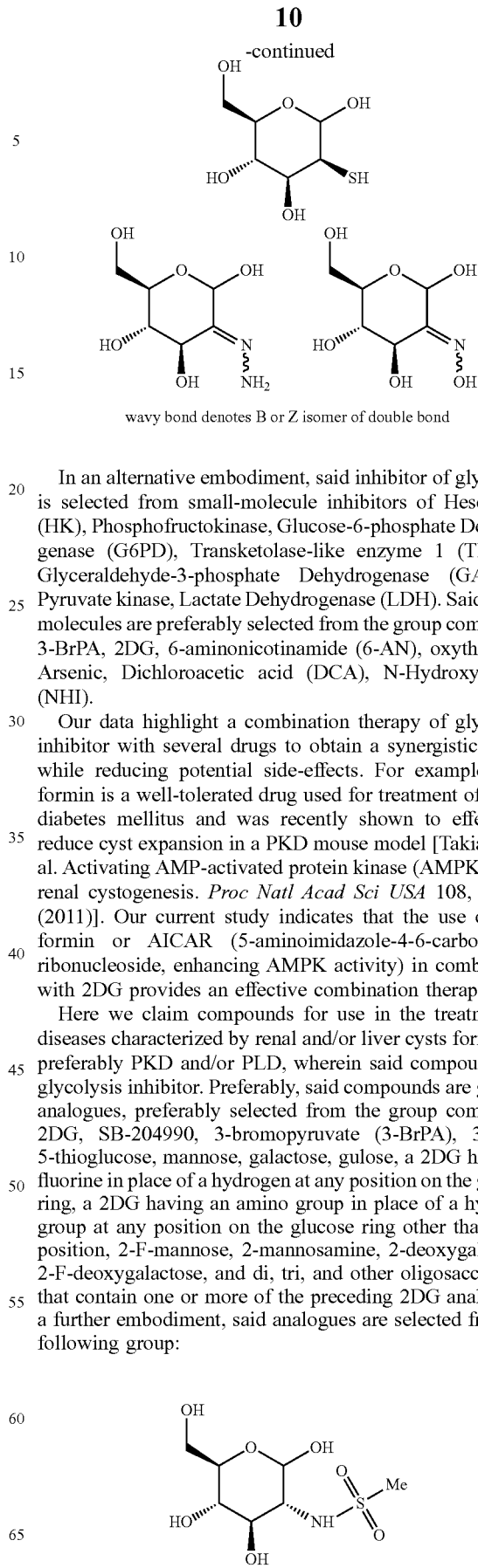

wavy bond denotes E or Z isomer of double bond

In an alternative embodiment, said inhibitor of glycolysis is selected from small-molecule inhibitors of Hexokinase (HK), Phosphofructokinase, Glucose-6-phosphate Dehydrogenase (G6PD), Transketolase-like enzyme 1 (TKTL1), Glyceraldehyde-3-phosphate Dehydrogenase (GAPDH), Pyruvate kinase, Lactate Dehydrogenase (LDH). Said small-molecules are preferably selected from the group comprising 3-BrPA, 2DG, 6-aminonicotinamide (6-AN), oxythiamine, Arsenic, Dichloroacetic acid (DCA), N-Hydroxyindoles (NHI).

Our data highlight a combination therapy of glycolysis inhibitor with several drugs to obtain a synergistic effects while reducing potential side-effects. For example, metformin is a well-tolerated drug used for treatment of type 2 diabetes mellitus and was recently shown to effectively reduce cyst expansion in a PKD mouse model [Takiar, V. et al. Activating AMP-activated protein kinase (AMPK) slows renal cystogenesis. *Proc Natl Acad Sci USA* 108, 2462-7 (2011)]. Our current study indicates that the use of metformin or AICAR (5-aminoimidazole-4-6-carboxamide ribonucleoside, enhancing AMPK activity) in combination with 2DG provides an effective combination therapy.

Here we claim compounds for use in the treatment of diseases characterized by renal and/or liver cysts formation, preferably PKD and/or PLD, wherein said compounds are glycolysis inhibitor. Preferably, said compounds are glucose analogues, preferably selected from the group comprising 2DG, SB-204990, 3-bromopyruvate (3-BrPA), 3-BrOP, 5-thioglucose, mannose, galactose, gulose, a 2DG having a fluorine in place of a hydrogen at any position on the glucose ring, a 2DG having an amino group in place of a hydroxyl group at any position on the glucose ring other than the 6 position, 2-F-mannose, 2-mannosamine, 2-deoxygalactose, 2-F-deoxygalactose, and di, tri, and other oligosaccharides that contain one or more of the preceding 2DG analogs. In a further embodiment, said analogues are selected from the following group:

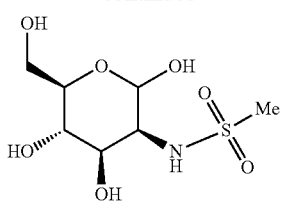
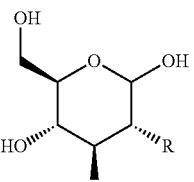
R = CH₃, CH₂F, CHF₂, CF₃
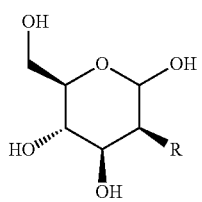
R = CH₃, CH₂F, CHF₂, CF₃
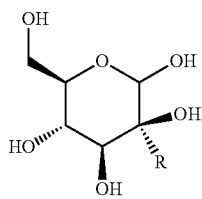
R = CH₃, CH₂F, CHF₂, CF₃
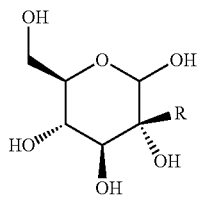
R = CH₃, CH₂F, CHF₂, CF₃
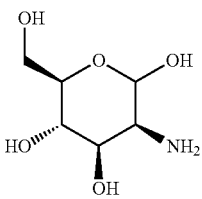
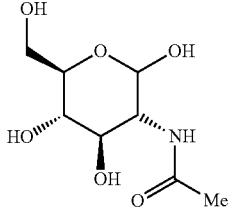
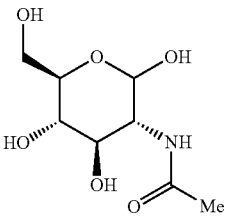
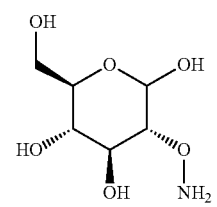
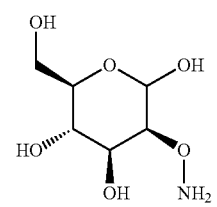
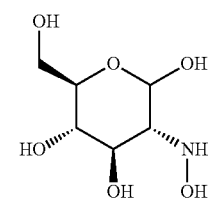
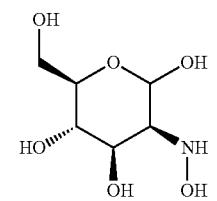
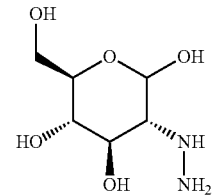
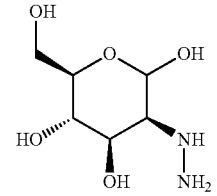
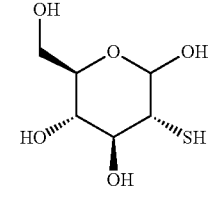

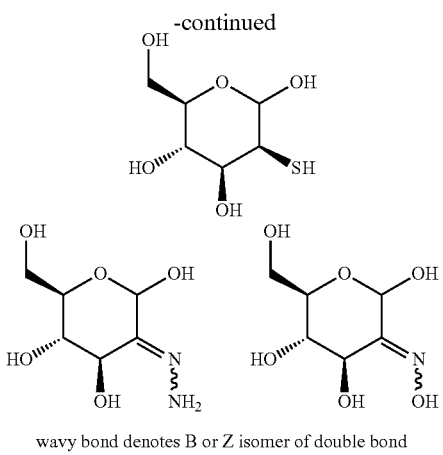

wavy bond denotes E or Z isomer of double bond

In an alternative embodiment, said compounds for use in the treatment of diseases characterized by renal and/or liver cysts formation, preferably PKD and/or PLD, are inhibitor of glycolysis, selected from small-molecule inhibitors of Hesokinase (HK), Phosphofructokinase, Glucose-6-phosphate Dehydrogenase (G6PD), Transketolase-like enzyme 1 (TKTL1), Glyceraldehyde-3-phosphate Dehydrogenase (GAPDH), Pyruvate kinase, Lactate Dehydrogenase (LDH). Said small-molecules are preferably selected from the group comprising 3-BrPA, 2DG, 6-aminonicotinamide (6-AN), oxythiamine, Arsenic, Dichloroacetic acid (DCA), N-Hydroxyindoles (NHI).

In a further embodiment, the present invention is related to a pharmaceutical composition comprising at least one glycolysis inhibitor selected among glucose analogues or in the group comprising small-molecule inhibitors of Hesokinase (HK), Phosphofructokinase, Glucose-6-phosphate Dehydrogenase (G6PD), Transketolase-like enzyme 1 (TKTL1), Glyceraldehyde-3-phosphate Dehydrogenase (GAPDH), Pyruvate kinase, Lactate Dehydrogenase (LDH).

In a further embodiment, said at least one glycolysis inhibitor selected among glucose analogues or in the group comprising small-molecule inhibitors of Hesokinase (HK), Phosphofructokinase, Glucose-6-phosphate Dehydrogenase (G6PD), Transketolase-like enzyme 1 (TKTL1), Glyceraldehyde-3-phosphate Dehydrogenase (GAPDH), Pyruvate kinase, Lactate Dehydrogenase (LDH) is associated with at least one ERK inhibitor, preferably selected in the group comprising PD98059 and UO126 and/or at least one B-Raf inhibitor, preferably selected in the group comprising Vemurafenib (RG7204), GDC-0879, PLX-4720 and Sorafenib, and/or at least one mTOR inhibitor preferably selected in the group comprising rapamycin, metformin and/or AICAR.

The pharmaceutical compositions of the present invention can be formulated in combination with pharmaceutically acceptable carriers, excipients, stabilizers, diluents or biologically compatible vehicles suitable for administration to a subject (for example, physiological saline). Pharmaceutical compositions of the invention include all formulations wherein said compounds are contained in therapeutically effective amount, that is, an amount effective to achieve the medically desirable result in the treated subject. Pharmaceutical compositions may be formulated in any acceptable way to meet the needs of the mode of administration. The use of biomaterials and other polymers for drug delivery, as well the different techniques and models to validate a specific mode of administration, are disclosed in literature. Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes. Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, ethyloleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions which can be administered rectally include suppositories. As well known in the medical arts and determinable by one of skill in the art, dosages for any one patient depends upon many factors, including the patient's size, body surface area, age, the particular compound to be administered, sex, time and route of administration, general health, and other drugs being administered concurrently, if any, and the nature of the effect desired. The total dose required for each treatment may be administered by multiple doses or in a single dose. The pharmaceutical composition of the present invention may be administered alone or in conjunction with other therapeutics directed to the condition, or directed to other symptoms of the condition.

For a therapy comprising the administration of an inhibitor of glycolysis as defined above, the persons of skill in the art will understand that an effective amount of the compounds used in the methods of the invention can be determined by routine experimentation. It is a further object of the invention a method of treatment of a pathology characterized by renal and/or liver cysts formation comprising administering an effective amount of at least one inhibitor of glycolysis as defined above, per se or in combination with at least one ERK inhibitor, and/or at least one B-Raf inhibitor, and/or at least one mTOR inhibitor or of a pharmaceutical composition as defined above in a subject in need thereof.

In a further preferred embodiment, said inhibitor of glycolysis is 2DG. 2DG is administered in a subject in need thereof at a dosage comprised in the range 20-250 mg/kg, or 30-200 mg/kg, or 40-150 mg/kg, or 45-100 mg/kg, or 50-65 mg/kg, or about 60 mg/kg. 2DG is administered alone or optionally along with pharmaceutically acceptable carriers and excipients, in preformulated dosages. Preferably, the administration is chronic and 2DG is administered daily 5 days a week. The chronic administration of 2DG at the indicated dosage results in a decline of kidney volume increase and in a reduced renal function decline.

In a further embodiment, said 2DG is administered in combination with at least one ERK inhibitor, and/or at least one B-Raf inhibitor, and/or at least one mTOR inhibitor.

In a further embodiment, the present invention is related to a method to monitor treatment responses of PKD patients, comprising the step of evaluating over time the glycolysis in kidney cells, wherein a decrease in glycolysis is an index of a positive therapeutic effect. In a preferred embodiment, said method evaluates glycolysis by imaging uptake of 2-$^{18}$F-2-deoxyglucose (FDG) with positron emission tomography (PET).

Methods

Antibodies, Reagents, and Inhibitors

Antibodies anti-p-Akt 5473, anti-p-AMPK-Thr172; anti-AMPK, anti-p-S6RP Ser 235/236; anti-S6Rp; anti-p-ERK T202/Y204 and anti-ERK antibodies were from Cell Signaling Technology and used at 1:1000; anti-LC3 NB100 was from Novus Biologicals; anti-actin and anti-tubulin antibodies were from Sigma Aldrich and used at 1:5000. Anti-ki67 was from Novocastra and was used at 1:400. UO126 and rapamycin (Cell Signaling Technologies) were employed at final concentrations of 30 µM and 20 or 50 nM, respectively. AICAR and Metfomin (Sigma Aldrich) were used at the final concentration of 2 mM, oligomycin (Sigma Aldrich) was used at the final concentration of 30 µg/ml.

For experiments of glucose starvation the composition of the medium is: basic DMEM (Gibco) 2.3 g/L, Sodium Bicarbonate (Gibco) 3.7 g/L, L-glutamine 0,584 g/L (Gibco), serum (Euroclone), 10%, pen-strep 1% (Gibco) with or without glucose (Sigma) 4.5 g/L.

NMR and Metabolomic Profiling

For NMR analysis of the extracellular medium, 530 µl of cell culture medium were mixed with 60 µl of deuterated PBS solution containing DSS as chemical shift reference for both proton and carbon dimensions, and 10 µl of 1.2% NaN3 water solution. Final sample volume was 600 µl, containing 50 mM PBS, 0.02% NaN3 and 90 µM DSS. NMR spectra were acquired using a 600 MHz spectrometer (Bruker Avance 600 Ultra Shield™ Plus, Bruker BioSpin) equipped with a triple-resonance TCI cryoprobe with a z shielded pulsed-field gradient coil. All experiments were carried out at 298 K, spectrometer temperature was calibrated using pure methanol-d4 sample21. Sample temperature inside the spectrometer was equilibrated for minutes before data acquisition. For each sample noesygppr1d and Carr-Purcell-Meiboom-Gill T2 filter cpmgpr1d Bruker pulse sequences were acquired. For all experiments continuous water presaturation with a RF of Hz was applied during relaxation delay. Both the noesygppr1d and cpmgpr1d experiments were acquired with 80 scans, 98K complex data points, spectral width of 20 ppm, and relaxation delay of 6 s. A mixing time of 10 ms was used for the noesygppr1d experiment.

Prior Fourier Transformation FIDs were multiplied by an exponential function equivalent to 1.0 Hz line-broadening. Spectra were automatically phased; baseline corrected and referenced using the library Topspin AU program apk0.noe.

To facilitate metabolites identification we acquired 2D J-resolved $^1$H NMR experiments, 2D-$^1$H-$^1$H-TOCSY (Total Correlation spectroscopy) and 2D-$^1$H-$^{13}$CHSQC (Heteronuclear single quantum coherence). 2D J-resolved experiments were acquired with 12 FIDs, accumulated over 40 increments; spectral widths were set to 16.7 ppm and 78 Hz for F2 and F1, respectively; during the relaxation delay (2 s) the water signal was suppressed using presaturation. $^2$D-$^1$H-$^1$H-TOCSY experiments were acquired with a total of 8 FIDs for each of the 512 increments. Spectral widths were set to 12 ppm for both dimensions; water was suppressed with an excitation sculpting scheme, 2 s of relaxation delay was employed. $^2$D-$^1$H-$^{13}$C-HSQC spectra were acquired with a total of 44 FIDs for each of the 300 increments. Spectral widths were set to 16 and 185 ppm for $^1$H and $^{13}$C, respectively (with offsets equal to 4.7 and 75 ppm, respectively). The water signal was suppressed using a continuous wave presaturation during the 3 s of the relaxation delay.

Metabolites were identified using Metabominer [Xia, J.; Bjorndahl, T. C.; Tang, P.; Wishart, D. S., MetaboMiner-semi-automated identification of metabolites from 2D NMR spectra of complex biofluids. BMC Bioinformatics 2008, 9, 507] and CCPN Metabolomic project [The CCPN Metabolomics Project: a fast protocol for metabolite identification by 2D-NMR. Chignola F, Mari S, Stevens T J, Fogh R H, Mannella V, Boucher W, Musco G. Bioinformatics. 2011 Mar. 15; 27(6):885-6]. We identified and quantified 22 metabolites summarized in FIG. 10.

Metabolite Quantification

The NMR profiling strategy included, peaks assignment and integration to obtain metabolites concentrations. For metabolites quantification we took advantage of the combination of (a) the algorithm called GSD (global spectrum deconvolution), available in the Mnova software package of Mestrelab [Cobas, C.; Seoane, F.; Dominguez, S.; Sykora, S.; Davies, A. N. A new approach to improving automated analysis of proton NMRSpectrosc. Eur. 2010, 23 (1), 26-30] and (b) of a quantitative referencing strategy, known as PULCON [G. Wider, L. Dreier, Measuring Protein Concentrations by NMR Spectroscopy, JACS 128, 2571-2576 (2006)]. Combining the GSD algorithm with a PULCON script we deconvolved overlapping regions and performed absolute quantification also of metabolites with resonances in crowded spectral areas [Garcia-Manteiga J M, Mari S., Godejohann, Spraul M, Napoli C, Cenci S, Musco G and Sitia R, Metabolomics of B to plasma cell differentiation, J. Proteome Res. 2011, 10, 4165-4176].

ATP and Lactate Quantification

For ATP content evaluation, whole-cell extracts of control and treated MEFs cells were prepared by suspending pellets in lysis buffer as described in Distefano et al, 2009. Intracellular ATP quantification of lysates was measured on 250 ng of protein by luciferase activity as showed in the standard protocol present in the ATP Determination kit (Invitrogen). Medium of control and treated MEFs was taken after 24 h at 100% of confluence. The concentration of lactate using EnzyChrom™ L-lactate Assay Kit (BioAssay Systems) and quantified on the final number of cells.

Mitochondrial Transmembrane Potential ($\Delta\psi$m) assay

The mitochondrial transmembrane potential ($\Delta\psi$m) was assessed using the tetramethylrhodamine (TMRM, Invitrogen) and analyzing cells by time-lapse imaging and cytofluorimetrically. For FACS analysis, 24 hours after plating, cells were resuspended in phenol-red free HESS with 10 mM HEPES with 20 nM TMRM in the presence of multidrug resistance pump inhibitor cyclosporine H 2 mm and incubated for 30 min at 37° C. In parallel, cells were incubated with an uncoupling agent FCCP 4 µm to measure the specific mitochondria staining. TMRM fluorescence was measured by FACS analysis as described in Distefano et al, 2009. For quantitative real-time analysis of mitochondrial transmembrane potential, cells were incubated for 30 min at 37° C. in phenol-red free HBSS (Gibco) with 10 mM HEPES (Gibco), 20 nM TMRM, cyclosporine H 2 µM and 2 µg/ml Hoechst 33342. Images were acquired with IN CELL Analyser 1000 (LKT laboratories) before and after FCCP 4 µm was injected in a motorized way and sequential images were taken for TMRM and Hoechst in different regions of interest every 3 min and the images were automatically analyzed with IN CELL INVESTIGATOR ANALYSIS software (GE Healthcare) to define the TMRM intensity.

Proliferation and Apoptosis Assays

For proliferation assays immunostaining was carried our using an anti-Ki67 antibody followed by analysis. For cells, fluorescence was measured on triplicates of 300 cells using the microscope Axioplot (Zeiss). For kidney sections, pictures at 20× were taken using the camera Axio MRc5 (Zeiss) with the microscope Axioplan 2 (Zeiss), positive cells were counted on 6 sections for each group for each experiment using the ImageJ software.

For apoptosis assays cells were analyzed by the DeadEnd Flurometric transferase-mediated dUTP nick-end labeling (TUNEL) system kit (Promega) following the manufacturer's instructions.

Generation and 2DG Treatment of Pkd1$^{flox/-}$: Ksp-Cre Mice

Generation of Pkd1$^{flox/-}$:Ksp-Cre mice was previously described. Briefly, we crossed Pkd1$^{flox/flox29}$ and Pkd1$^{+/-}$: Ksp-Cre mice in pure C57/B16 genetic background. For treatments 2DG (Sigma-Aldrich) or vehicle (NaCl) were injected subcutaneously daily from P6 until P8 at 500 mg/kg.

2DG (Sigma-Aldrich) or vehicle (NaCl) were injected subcutaneously daily from P6 until P8 at 500 mg/kg.

Histology, Immunohistochemistry and Immunofluorescence

After sacrifice, kidneys were removed, washed in phosphate-buffered saline (PBS), weighed and fixed in 4% Para formaldehyde (PFA). After incubation in a sucrose in PBS gradient scale from 10% to 30% samples were incubated in 10% glycerol (Sigma) in a mixture of OCT (BIO-OPTICA) and sucrose 30%, finally embedded in OCT. Criostat sections were air-dried 1 h, rehydrated in PBS, incubated in Harris Hematoxylin 1:10 (Sigma Aldrich) for 2 min, washed, incubated in Eosin G (BIO-OPTICA) for 7 min, washed dehydrated and mounted in DEPEX (Sigma).

For Immunohistochemistry 10 µm cryosections were washed in Tween-0.1% in PBS (like all washes), fixed in PAF4%, permeabilized in Triton 0.1% in PBS, incubated in hydrogen peroxide 0.3% for 30 min, blocked for 1 h at room temperature with 5% Normal Goat Serum (Sigma Aldrich) 3% bovine serum albumin (BSA, Sigma) in phosphate-buffered saline, incubated O/N at 4° C. with the Antibody (ab) in blocking buffer diluted at 1:500. Sections were then incubated with the Dako EnVision+System-HRP (Dako). Staining is completed by an incubation with 3,3' diaminobenzidine tetrahydrochloride (DAB) DAB+Substrate Chromogen System (DakoCytomation) and counterstained with Harris Hematoxylin (Sigma Aldrich). diluted 1/10 for 3 min.

Immunofluorescence: Cells were fixed in PAF 4%, washed in PBS, permeabilized in PBS-Triton 0.2%, blocked with BSA 3% in PBS, incubated 45 min at 37° C. with the ab anti ki67 described above at 1/1000 in blocking, washed, incubated with the secondary antibody diluted at 1:1000 for 1 h.

Renal Cysts and Microarray Data Analysis

Renal cysts of different sizes were obtained from 5 polycystic kidneys. Minimally cystic tissue (MCT), which might have contained a few microscopic cysts from the renal cortex, was obtained as PKD control tissue from the same kidneys. Non-cancerous renal cortical tissue from 3 nephrectomized kidneys with isolated renal cell carcinoma was used as normal control tissue. The surgical technique, RNA extraction, purification, quality control, microarray hybridization, profiling and quality assessments have been described previously. After extraction with Absolutely RNA RT-PCR Miniprep Kit (Stratagene), 50 to 100 ng total RNA were labelled and hybridized onto GeneChip Human Genome U133 Plus 2.0 Array (Affymetrix) according to the manufacturer's protocol. Scanned raw data images were processed with GeneChip Operating Software (GCOS) 1.4.

Probe set signal intensities were extracted and normalized by the robust multi-array average algorithm, which can be found in the R package affy that can be downloaded from the Bioconductor project website (http://www.bioconductor.org). Microarray data are available at GEO website (accession number: GSE7869).

Statistical Analysis of the Microarrays

Gene set enrichment analysis (GSEA) (Subramanian, A., Tamayo, P., Mootha, V. K., Mukherjee, S., Ebert, B. L., Gillette, M. A., Paulovich, A., Pomeroy, S. L., Golub, T. R., Lander, E. S. et al. (2005) Gene set enrichment analysis: a knowledge-based approach for interpreting genome-wide expression profiles. *Proc Natl Acad Sci USA*, 102, 15545-50) and Significance analysis of microarrays (SAM) (Tusher, V. G., Tibshirani, R. and Chu, G. (2001) Significance analysis of microarrays applied to the ionizing radiation response. *Proc Natl Acad Sci USA*, 98, 5116-21.) were used to identify differentially expressed gene pathways and individual genes, respectively. We defined differentially expressed pathways by a NOM P-value≤0.05 with a false discovery rate (FDR)≤0.25, and used FDR≤0.5% for the individual gene comparisons.

Western Blot Analysis

For western blot analysis, the cells were lysed [lysis buffer: 250 mM sucrose, 20 mM imidazole and 1 mM EDTA, pH 7.4, 0.5% Triton-X 100, supplemented with Protease Inhibitors Cocktail (Amersham) and phosphatase inhibitors (1 mM final of glycerophosphate, sodium orthovanadate and sodium fluoride)]. Total lysates were quantified and Laemmli buffer was added to reach a 1× final concentration. Proteins were resolved in a SDS-PAGE gel and transferred onto PVDF membranes. Next, 5% milk in TBS-T was used for blocking and for secondary antibody incubations, while 2% BSA in TBS-T was used for incubations with primary antibodies. HRP-conjugated secondary antibodies (from Roche) were visualized using the ECL System (Amersham), which were mixed with Super-Femto ECL System from Pierce when necessary.

Realtime PCR Analysis

Total RNA was isolated from cells or whole kidneys using the RNAspin kit (GE Healthcare) and complementary DNA was obtained using oligo(dT) primers (Invitrogen) and Superscript II Reverse Transcriptase (Invitrogen). Quantitative real-time PCR was then performed in duplicates using LightCycler480 (Roche Molecular Diagnostics) using SYBR Green I master mix. The complete sequence of primers used is provided here below. The primers used for real time PCR analysis were the following:

```
beta actin
forward: 5'AGAAAATCTGGCACCACACC3' reverse: 5'CAGAGGCGTACAGGGATAGC3';

AldoA1/2
forward: 5'AGCAGAATGGCATTGTACCC3', reverse: 5'AAAGTGACCCCAGTGACAGC3',

HK1
forward: 5'TTTCATTGCACTGGATCTCG3' reverse: 5'CGTCTATTTTGGATTGTCGGC3',

Aldo C
forward: 5'GACCCCCGGCAAGGGCATTC3', reverse: 5'TGGTTTCCCCGTCGGTCCCA3';

Arbp
forward: 5'CTTCATTGTGGGAGCAGACA3', reverse: 5'TTCTCCAGAGCTGGGTTGTT3';

PDK1
forward: 5'GGCGGCTTTGTGATTTGTAT3' reverse: 5'ACCTGAATCGGGGGATAAAC3',
```

```
                        -continued
GAPDH
forward:  5'ACCACAGTCCATGCCATCAC3' reverse:  5'TCCACCACCCTGTTGCTGTA3'

Glut-1
forward:  5'GTCGGCCTCTTTGTTAATCG3' reverse:  5'CACATACATGGGCACAAAGC3'

Pkm2
forward:  5'GACTCTGCCCCCATCACGGC3' reverse:  5'GCCACCGCAACAGGACGGTA3';

G6PC
forward:  5'TTGCTGACCTGAGGAACGCCT3' reverse:  5'CAGGACCCACCAATACGGGCG3';

LDHA
forward:  5'AGAGCGGGAGGGCAGCTTTCT3' reverse:  5'GGGCAAGCTCATCCGCCAAGT3'.
```

The ΔCt method was used for quantification, and the β-actin gene was used respectively for normalization.

Glycolytic Flow In Vivo Analysis Using C13 Labeled Glucose

Litters ksp-cre: Pkd1$^{flox/-}$ and Pkd1$^{flox/+}$ were injected intracutaneously with C13 labeled glucose (sigma Aldrich) at 1000 mg/Kg. After 40 min, the mouse is sacrificed and the kidney is washed in PBS at 4° C. and immediately frozen.

Freeze kidneys were weights and directly lyophilized for hours. After lyophilization kidneys were weighted again and then polar metabolites were extracted from tissues using MeOH/CHC13 solvent extraction strategy. Polar phases were lyophilized for 24 hours. Lyophilized powder was resuspended in phosphate buffer 150 mM, with addition of about 100 uM DSS as internal chemical shift indicator, and sodium azide for sample preservation. Final volumes were 250 uL ad H2O/D2O ratio was kept to 90/10.

13C labeled lactate produced after sub ministration of 13C-glucose was detected by 1H-13C-HSQC NMR. NMR experiments were performed at 25° C. on a Bruker Avance 600 Ultra Shield™ Plus 600 MHz spectrometer equipped with triple resonance cryoprobe (TCI) and pulsed field gradients. Spectra were acquired under the same experimental conditions among for all the samples analyzed. We used 512 increments in the direct dimension (f2) and 400 in the indirect one (f1). Spectral widths were 11 ppm in f2 and 200 in f1. Relaxation delay was settled to 3 s, and a water presaturation scheme was used.

A 13C-glucose standard solution of known concentration was prepared under the same condition of buffering and H2O/D2O ratio. Glucose peak at position 2 (chemical shifts 3.15 ppm and 75 ppm) was used for calibration between peak volume and absolute concentration. This calibration factor was applied for the quantification of 13C-lactate methyl peak centered at 1.30 ppm and 23 ppm. 13C-lactate concentration were found to be 0.26 mM+−0.1 for wt/mg of kidney dry weight.

Cystic Index

A grid of squares 13.625 μm large was applied to sections of kidneys stained with Hematoxylin-Eosin. Each cross is marked with a dot, number of dots inside the lumen are counted on three litters (218 000 μm$^2$ for each). The degree of dilatation is determined according to Lu et al., 1999 [32]:1 dot: normal tubules; 2 dots: dilatated tubules; 3-9 dots: Small cysts; ≥10 dots: Cysts.

Statistics

Mann Whitney test was used to analyze the difference of distribution between groups shown from b to e. Statistical analysis of real time and Jablonski indexes was performed by applying t test after one-way analysis of variance (ANOVA). The statistics were performed using the Graph-Pad Prism software.

Electron Microscopy

Cell culture monolayers were fixed for 15 min at 4° C. with PAF 4% and 2.5% glutaraldehyde in 125 mM cacodylate buffer. The monolayers were detached by rubber and centrifuged at high speed. The pellet was post-fixed (1 hour) with 2% OsO4 in 125 mM cacodylate buffer, was washed, dehydrated and embedded in Epon. Conventional thin sections were collect on uncoated grids, stained with uranil and lead citrate and examined in a Leo912 electron microscope.

Statistical Analysis

For statistical analysis of the NMR data, PCA analysis was performed using R-statistical open source software (http://www.r-project.org/) using in-house statistical package called MUMA (free available upon request). In particular, for statistical analysis we used the metabolites concentrations and applied the Pareto scaling of the variables prior to principal component analysis (PCA), a multivariate unsupervised statistical technique. PCA gives a global view of the systematic variation of the data while reducing its dimensionality to few principal components (PC), which account for a large amount of the total variance between the NMR fingerprints. The final aim of PCA is to enable easy visualization of any clustering or similarity of the various samples. The results of PCA are presented in terms of score (FIG. 7b) and loading plots (FIG. 7c). Samples with a similar metabolic footprint tend to cluster together in score plots. Each PC is a weighted linear combination of the original descriptors and this information is shown in a loading plot.

For other in vitro and in vivo studies Statistical analysis was performed by applying either an unpaired T-test or a one-way analysis of variance (ANOVA) followed by Student's t test. The statistical analysis tool employed as well as the precise P value obtained is in the legends. ns>0.05; *P≤0.05; , P≤0.0001; *, P≤0.0001.

For the microarrays studies, differentially expressed pathways were defined by a NOM P-value≤0.05 with a false discovery rate (FDR)≤0.25, and used FDR≤0.5% for the individual gene comparisons.

The invention claimed is:

1. A method of treating autosomal dominant polycystic kidney disease (ADPKD) in a subject in need thereof, comprising administering an effective amount of a pharmaceutical composition comprising 2-deoxyglucose (2DG).

2. A method of treatment according to claim 1, wherein said 2DG is administered at a dosage in the range 20-250 mg/kg.

3. A method of treatment according to claim 1, wherein said 2DG is administered at a dosage in the range 30-200 mg/kg.

4. A method of treatment according to claim 1, wherein said 2DG is administered at a dosage in the range 40-150 mg/kg.

5. A method of treatment according to claim 1, wherein said 2DG is administered at a dosage in the range 45-100 mg/kg.

6. A method of treatment according to claim 1, wherein said 2DG is administered at a dosage in the range 50-65 mg/kg.

7. A method of treatment according to claim 1, wherein said 2DG is administered at a dosage of about 60 mg/kg.

8. The method of treatment according to claim 1, wherein said pharmaceutical composition further comprises at least one extracellular signal-regulated kinases (ERK) inhibitor selected from 2-(2-Amino-3-methoxyphenyl)-4H-1-benzopyran-4-one (PD98059), 1,4-Diamino-2,3-dicyano-1,4-bis[2-aminophenylthio]butadiene (UO126) or combinations thereof.

9. The method of treatment according to claim 1, wherein said pharmaceutical composition further comprises at least one Serine/threonine-protein kinase (B-raf) inhibitor selected from Vemurafenib (RG7204), (E)-2,3-Dihydro-5-[1-(2-hydroxyethyl)-3-(4-pyridinyl)-IH-pyrazol-4-yl]-IH-inden-1-one oxime (GDC-0879), N-[3-[(5-chloro-1H-pyrrolo[2,3 b]pyridin-3-yl)carbonyl]-2,4-difluorophenyl]-1 propanesulfonamide (PLX-4720), Sorafenib or combinations thereof.

10. The method of treatment according to claim 1, wherein said pharmaceutical composition further comprises at least one mTOR inhibitor selected from rapamycin, metformin, 5-aminoimidazole-4-6-carboxamide ribunocleoside (AICAR) or combinations thereof.

11. The method of treatment according to claim 1, wherein said pharmaceutical composition further comprises at least one compound selected from the group comprising 2-(2-Amino-3-methoxyphenyl)-4H-1-benzopyran-4-one (PD98059), 1,4-Diamino-2,3-dicyano-1,4-bis[2-aminophenylthio]butadiene (UO126), Vemurafenib (RG7204), E)-2,3-Dihydro-5-[1-(2-hydroxyethyl)-3-(4-pyridinyl)-IH-pyrazol-4-yl]-IH-inden-1-one oxime (GDC-0879), N-[3-[(5-chloro-1H-pyrrolo[2,3 b]pyridin-3-yl)carbonyl]-2,4-difluorophenyl]-1 propanesulfonamide (PLX-4720), Sorafenib, rapamycin, metformin, 5-aminoimidazole-4-6-carboxamide ribonucleoside (AICAR) or combinations thereof.

* * * * *